United States Patent [19]

Boigegrain et al.

[11] Patent Number: 5,656,631
[45] Date of Patent: Aug. 12, 1997

[54] PYRIDAZINE DERIVATIVES

[75] Inventors: Robert Boigegrain, Clapiers; Roger Brodin, Montpellier; Jean Paul Kan, Clapiers; Dominique Olliero, Montpellier; Camille Georges Wermuth, Strasbourg; Jean-Jacques Bourguignon, Hipsheim; Paul Worms, St Gely du Fesc, all of France

[73] Assignee: Sanofi, Paris, France

[21] Appl. No.: 473,580

[22] Filed: Jun. 7, 1995

Related U.S. Application Data

[60] Division of Ser. No. 964,901, Oct. 22, 1992, Pat. No. 5,461,053, which is a continuation-in-part of Ser. No. 737,654, Jul. 30, 1991, abandoned, and Ser. No. 871,505, Apr. 21, 1992, abandoned, which is a continuation-in-part of Ser. No. 475,489, Feb. 7, 1990, abandoned, and Ser. No. 615,373, Nov. 19, 1990, abandoned.

[30] Foreign Application Priority Data

| Feb. 7, 1989 | [FR] | France | 89 01547 |
| Feb. 7, 1989 | [FR] | France | 89 01548 |
| Nov. 17, 1989 | [FR] | France | 89 15137 |
| Jun. 15, 1990 | [FR] | France | 90 07533 |
| Jul. 31, 1990 | [FR] | France | 90 09777 |

[51] Int. Cl.$^6$ .................... A61K 31/50; C07D 237/20
[52] U.S. Cl. .................... 514/252; 514/253; 544/238
[58] Field of Search .................... 514/252, 253; 544/238

[56] References Cited

U.S. PATENT DOCUMENTS

| 4,508,720 | 4/1985 | Kan et al. | 544/224 |
| 4,514,397 | 4/1985 | Wermuth | 514/247 |
| 4,524,070 | 6/1985 | Kan et al. | 544/114 |
| 4,624,952 | 11/1986 | Biziere et al. | 514/247 |
| 4,721,711 | 1/1988 | Chambon et al. | 514/247 |
| 5,081,119 | 1/1992 | Boigegrain et al. | 514/247 |
| 5,276,036 | 1/1994 | Bourguignon et al. | 514/247 |
| 5,461,053 | 10/1995 | Boigegrain et al. | 514/247 |

*Primary Examiner*—Donald G. Daus
*Attorney, Agent, or Firm*—Bacon & Thomas

[57] ABSTRACT

The present invention relates to pyridazine derivatives of formula:

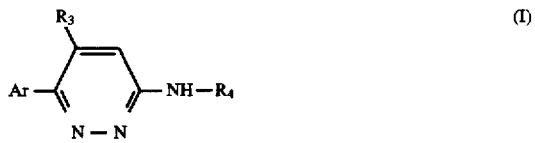

(I)

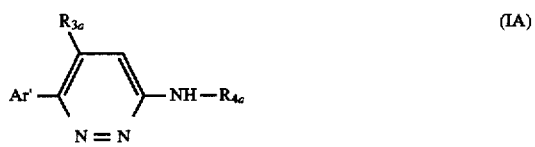

(IA)

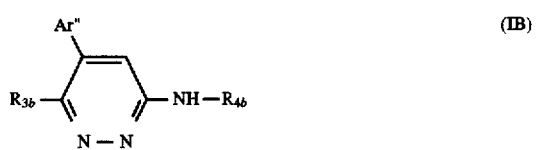

(IB)

which are useful as ligands of cholinergic receptors, in particular, receptors of the $M_1$ type.

18 Claims, No Drawings

PYRIDAZINE DERIVATIVES

This application is a Division of application Ser. No. 07/964,901, filed Oct. 22, 1992, now U.S. Pat. No. 5,461,053 which is a continuation-in-part of application Ser. No. 07/737,654, filed on Jul. 30, 1991, now abandoned, and application Ser. No. 07/871,505, filed on Apr. 21, 1992, now abandoned, which is a continuation-in-part of application Ser. No. 07/475,489, filed on Feb. 7, 1990, now abandoned, and application Ser. No. 07/615,373, filed on Nov. 19, 1990, now abandoned.

For many years pyridazine derivatives have been suggested as medicines, in particular medicines active on the cardiovascular system or on the central nervous system.

In particular, French patent 2 510 998 and European patent 72 726 disclose pyridazine derivatives variously substituted on the pyridazine ring and all bearing at position 3 an amine substituent of the type

in which X and Y independently represent hydrogen, alkyl or form together with the nitrogen atom to which they are attached a heterocycle such as morpholine.

All of these compounds exhibit an activity on the central nervous system as antidepressants.

According to one aspect of the present invention, novel derivatives of pyridazine have now been discovered which have lost their antidepressant activity and acquired a useful activity as ligands of cholinerzic receptors, in particular receptors of the $M_1$ type.

In accordance with a first feature, the object of the present invention is novel derivatives of pyridazine corresponding to the formula:

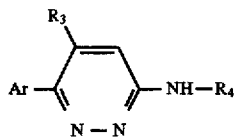

in which

Ar represents a phenyl group substituted by $R_1$ and $R_2$ or a heterocyclic radical such as a pyridyl group, unsubstituted or substituted by methyl or methoxy, or a thienyl group, unsubstituted or substituted by chlorine, methyl or methoxy;

$R_1$ and $R_2$ each independently denotes hydrogen, halogen, trifluoromethyl hydroxy, $C_1$–$C_4$ alkoxy or $C_1$–$C_4$ alkyl;

$R_3$ represents a $C_1$–$C_4$ linear or branched alkyl, $C_3$–$C_7$ cycloalkyl, benzyl, phenethyl or the Ar' radical, Ar' being phenyl substituted by $R_1$ and $R_2$;

$R_4$ represents:

a

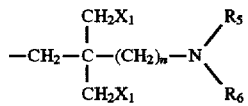

group, with n=0 or 1 in which $X_1$ represents hydrogen or methyl;

$R_5$ represents a $C_1$–$C_6$ linear alkyl group;

$R_6$ represents a $C_1$–$C_6$ linear alkyl group, or $R_5$ and $R_6$ also constitute together with the nitrogen atom to which they are attached a heterocycle selected from morpholine, pyrrolidine or piperidine; as well as their salts with organic or mineral acids.

Preferentially, Ar represents phenyl, unsubstituted or monosubstituted at position 2, more particularly Ar represents a group selected from phenyl, 2-halo-phenyl, in particular 2-chloro-phenyl, 2-methoxy-phenyl or 2-hydroxyophenyl, $R_3$ represents phenyl or n-propyl, $R_5$ and $R_6$ each represents ethyl, n=0 and $X_1$=H.

The following compounds are particularly preferred:
- 3-(2-diethylamino-2-methyl-propyl)amino-6-phenyl-5-propyl-pyridazine and its salts;
- 3-(2-diethylamino-2-methyl-propyl)amino-5,6-diphenylpyridazine and its salts.

The salts of the compounds of formula I according to the present invention includes those with both mineral and organic acids which enable the compounds of formula I to be separated or suitably crystallized, such as picric acid or oxalic acid, those which form pharmaceutically acceptable salts such as the hydrochloride, hydrobromide, sulfate, hydrogen sulfate, dihydrogen phosphate, methane sulfonate, methyl sulfate, maleate, fumerate, 2-naphthalene sulfonate.

In accordance with a second feature, the present invention relates to a process for the preparation of the compounds of formula (I).

According to the present invention, the process for the preparation of the compounds of formula (I) is characterized in that an amine $R_4NH_2$ is reacted with a 6-chloro pyridazine of formula:

in which Ar and $R_3$ have the meanings indicated above for (I) and, optionally, the compound thus obtained is converted into a salt with a mineral or organic acid.

The substitution reaction of the 6-chloro pyridazine (II) by the amine $R_4NH_2$ is carried out between 100° and 150° C., optionally in the presence of ammonium chloride. The reaction is performed without solvent or in the presence of an inert solvent such as n-butanol. The product (I) is isolated by extraction and purified, for example, by chromatography.

The product of formula I thus obtained is isolated in the form of the free base or a salt according to standard techniques.

When the compound of formula I is obtained in the form of the free base, salt formation is carried out by treatment with the selected acid in an organic solvent. By treatment of the free base, dissolved for example in an alcohol such as isopropanol, with a solution of the selected acid in the same solvent, the corresponding salt is obtained which is isolated according to standard techniques. In this way, the hydrochloride, the hydrobromide, the sulfate, the hydrogen sulfate, the dihydrogen phosphate, the methane sulfonate, the methyl sulfate, the oxalate, the maleate, the fumarate and the 2-naphtnalene sulfonate are prepared.

At the end of the reaction, the compound of formula I may be isolated in the form of one of its salts, for example the hydrochloride; in this case, if necessary, the free base may be prepared by neutralization of the said salt with a mineral or organic base such as sodium hydroxide or triethylamine or an alkali metal carbonate or bicarbonate such as sodium or potassium carbonate or bicarbonate.

When $R_1$ and/or $R_2$ represent a hydroxyl group, the compound according to the invention is obtained starting from compound (I) in which $R_1$ and/or $R_2$ denote alkoxy and all of the other substituents have the above definitions, by dealkylation using known methods.

The 6-chloro pyridazines (II), used as starting materials, are prepared from the corresponding 2H-pyridazin-3-ones (III) by reaction with an excess of hot phosphorus oxychloride in the absence of a solvent or in the presence of an inert solvent such as acetonitrile, according to the following reaction scheme:

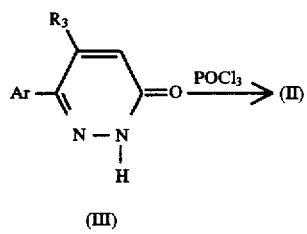

The 2H-pyridazin-3-ones (III) are known or prepared by known methods.

Thus, when $R_3$ is a Ar' radical, the 2H-pyridazin-3-ones are obtained according to the method described by P. SCHMIDT et al. in Helv. Chim. Acta, 1954, 15, 134–140, starting from malonic acid diethyl ester and a hydrazone derivative according to the following reaction scheme:

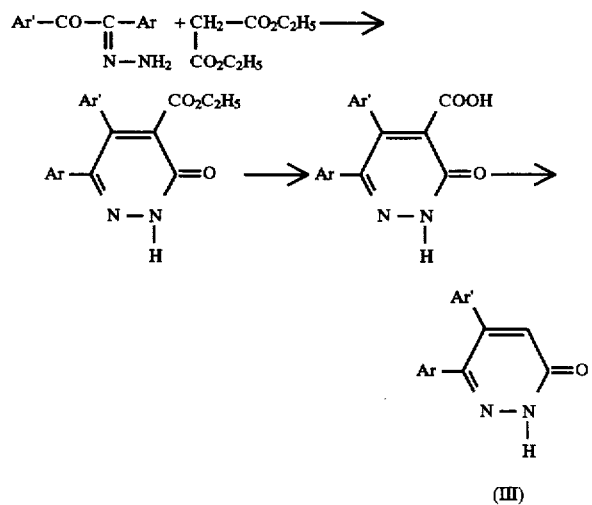

When $R_3$ represents an alkyl or cycloalkyl radical, the compounds (III) are prepared from a ketone Ar—CO—CH$_2$R$_3$ (1):

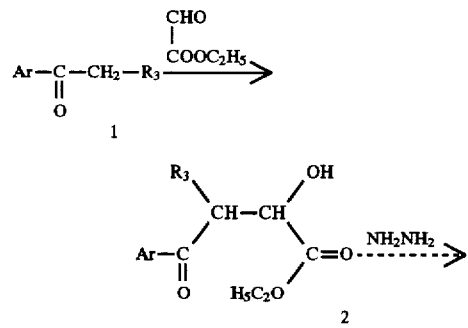

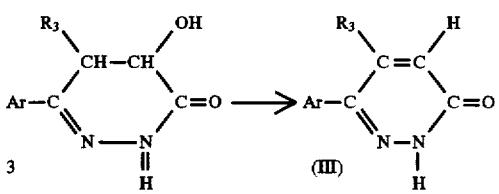

The hydroxy keto ester 2 is obtained from the ketone 1 by heating it with ethyl glyoxylate at a temperature between 30° and 140° C. The crude reaction mixture is then taken up in an inert solvent such as n-butanol and hydrazine hydrate is added. By heating at reflux for 24 hours, the 4,5-dihydro 4-hydroxy pyridazin-3-one 3 is obtained which, when heated in an acidic medium, leads by dehydration to the 2H-pyridazin-3-one (III).

The amines $R_4NH_2$ are known or prepared by known methods. Thus, when n=0, they may be prepared from a cyano derivative of formula:

By reaction with an amine $HNR_5R_6$ by heating at a temperature between 40° and 80° C., optionally in the presence of a salt of a strong acid such as sodium sulfate or magnesium sulfate, a compound of formula:

is first prepared, then this compound is hydrated by reaction with a strong acid such as hot sulfuric acid in order to produce the corresponding amide:

Finally, reduction by heating with a metal hydride such as boron hydride or lithium aluminium hydride leads to the formation of the amine $R_4NH_2$.

When n=0, the amine $R_4NH_2$ may also be prepared from a chloronitroso derivative (VII) according to the procedure described in J. Prakt. Chem., 1978, 320 (3), 433–451.

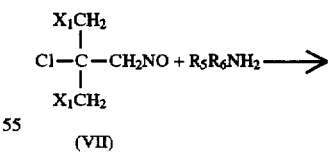

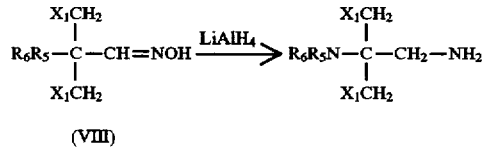

The compound of formula (VII) may be used in the form of a dimer (VIIa) which is obtained by reaction of nitrosyl chloride with the appropriate olefin (IX) according to the procedure described in J. Prakt. Chem., 1965, 29 (4), 123.

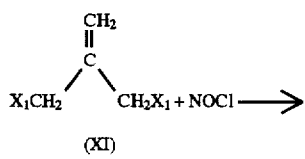

(XI)

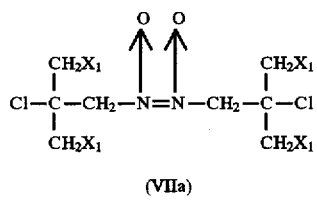

(VIIa)

Finally, when n=1, the amine $R_4NH_2$ may be prepared according to the method described in Beilstein 4 (3), 596, i.e. by reaction of lithium aluminium hydride on the oxime (X):

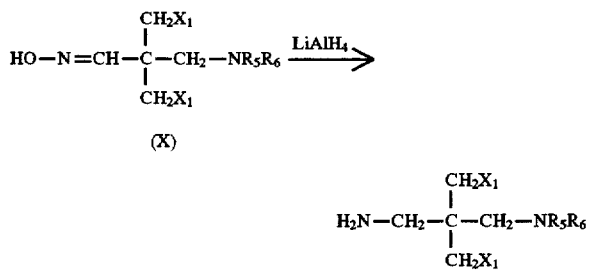

The amine $NH_2$—$CH_2C(CH_3)_2$—$CH_2$—$N(CH_3)_2$ is commercially available.

The following examples illustrate the invention without in any way limiting it. The compounds are characterized by their melting point (m.p.) expressed in degrees centigrade.

EXAMPLE 1

3-(2-diethylamino-2-methyl-propyl)amino-6-phenyl-5-propyl-pyridazine sesquifumarate: SR 46559 A.

A) 6-chloro-3-phenyl-4-propyl-pyridazine.

1. Ethyl 2-hydroxy-4-oxo-4-phenyl-3-propyl-butyrate.

A mixture of 48.67 g of valerophenone and 45.94 g of ethyl glyoxylate is heated at 120° C. for 15 hours.

The crude reaction product is used as such in the following step.

2. 6-phenyl-5-propyl-2H-pyridazin-3-one.

The crude product obtained above is dissolved in 450 ml of n-butanol, then 30 g of hydrazine hydrate are added and the mixture is heated at reflux for 24 hours.

The n-butanol is evaporated under vacuum. The residue is taken up in a mixture of 300 ml of acetic acid and 30 ml of concentrated hydrochloric acid. The mixture is heated at 100° C. for 3 hours. The solution is poured into cold water and the product is left to crystallize.

The solid is filtered off and dried.

Weight: 44 g M.p.: 160° C.

Yield: 69%

3. 6-chloro-3-phenyl-4-propyl-pyridazine.

250 ml of phosphorus oxychloride are added to 44 g of pyridazinone obtained above and the mixture is heated at 80° C. for 4 hours. After being left to stand overnight at room temperature, the reaction mixture is concentrated to ¾ and then poured slowly onto ice. The mixture is extracted twice with 300 ml of dichloromethane, the extracts are dried over sodium sulfate and concentrated. Chromatography on silica is then carried out by eluting with an ethyl acetate-methylene chloride mixture (50/50 v/v).

After recrystallization from isopropyl ether, 43.7 g of the expected product are obtained.

M.p.: 60° C.

Yield: 92%.

B) Preparation of 2-diethylamino-2-methyl-propylamine.

1. 2-diethylamino-2-methyl-propionitrile.

85.1 g of the cyanohydrin of distilled acetone and 73.1 g of diethylamine are mixed. 85.7 g of magnesium sulfate are added and the mixture is heated under gentle reflux for 20 hours with stirring. The sulfate mass which is formed is filtered off and washed with ether. The filtrate is concentrated and then distilled.

86.6 g of the expected product are recovered.

Yield: 62%

B.p.=68°–70° C. at 15 mm of mercury.

2. 2-diethylamino 2-methyl propionamide.

To 95.9 g of the nitrile prepared in the preceding step 450 ml of sulfuric acid and 70 ml of water are added with stirring and the mixture is heated on an oil bath at 100°–110° C. for 2 hours. The reaction mixture is poured slowly during one hour into 1.4 l of a 20% ammonia solution and 400 ml of water cooled in a Dry Ice/acetone bath. The mixture is extracted 3 times with 600 ml of methylene chloride, the extracts are dried over sodium sulfate and concentrated.

The expected product is obtained by distillation.

Weight: 102.5 g

Yield: 95%

B.p.: 134°–139° C. at 15 mm of mercury.

3. 2-diethylamino-2-methyl-propylamine.

A mixture containing 52.4 g of the amide prepared in the preceding step and 60 ml of tetrahydrofuran are heated at 45°–50° C. 86 ml of the borane-dimethylsulfide complex are added under an atmosphere of nitrogen during one hour and heating is continued for 3 hours on an oil bath at 80°–85° C.

After being left overnight at room temperature, the mixture is cooled in an ice bath, then 315 ml of 6N hydrochloric acid are added slowly during 3 hours and the mixture is heated again at 135° C. for 3 hours. After being left overnight at room temperature, the reaction mixture is cooled whilst 200 ml of 30% sodium hydroxide are added. The mixture is extracted 3 times with 250 ml of ether, the extracts are dried over sodium sulfate and concentrated.

The expected product is obtained by distillation.

Weight: 23 g

Yield: 48%

B.p.=71°–73° C. at 15 mm of mercury.

C) SR 46559 A

A mixture of 2.5 g of the chloro derivative obtained above in step A and 4.6 g of the diamine obtained in step B are heated at 120° C. overnight. 150 ml of ethyl acetate are added, then the mixture is extracted twice with 50 ml of hydrochloric acid. The mixture is then made alkaline by the addition of 50 ml of 30% sodium hydroxide and then extracted with ethyl acetate. The extracts are washed with dilute salt solution, dried over sodium sulfate and concentrated. Chromatography on alumina is carried out by eluting with a methylene chloride-ethyl acetate mixture (70/30, v/v).

3.2 g of an oil is obtained which crystallizes.

M.p.=75°–77° C.

Yield: 87%

Sesquifumarate 3.1 g of the base obtained in the preceding step are taken up in 50 ml of acetone and 1.6 g of fumaric acid in 150 ml of acetone are added. The mixture is filtered hot. The total volume recovered (175 ml) is concentrated to 130 ml. The product is allowed to crystallize, the crystals are filtered off and then washed with acetone.

4.1 g of the expected product are obtained.

Overall yield of step C=74%

M.p.=151° C.

EXAMPLE 2

SR 46559 A

A) 6-chloro-3-phenyl-4-propyl-pyridazine, described in example 1.

B) 2-diethylamino-2-methyl-propylamine.

1. Preparation of the compound of formula (VII a) with $X_1$=H.

47.14 g of isobutylene are dissolved in 150 ml of n-heptane, the mixture is cooled to a temperature between −10° and −20° C. and 50 g of nitrosyl chloride are added. The temperature is allowed to rise (+5° C.) during one and a half hours, then the temperature is brought to between 10° C. and 20° C. and the mixture is stirred for one and a half hours. The precipitate formed is filtered off, washed with heptane and then dried.

M.p.=102°–104° C.

m=64 g

2. Preparation of the compound of formula VIII: $X_1$=H; $R_5$=$R_6$=$C_2H_5$ 21.7 g of the compound prepared in the preceding step are suspended in 150 ml of absolute alcohol, 39.17 g of diethylamine are added and the mixture is heated at 60° C. for 6 hours. An oil is obtained which solidifies.

m=19.5 g

M.p.<50° C.

3. 2-diethylamino-2-methyl-propylamine 7.01 g of lithium aluminium hydride are added to 50 ml of an ethereal solution of the compound obtained in the preceding step during 1 hour. After being stirred for one and a half hours at room temperature, the mixture is refluxed for 4 hours. While the mixture is maintained between 0° C. and −10° C., 7.1 ml of water are added during 1 hour, 7.1 ml of sodium hydroxide during 30 minutes and 21.3 ml of water during 30 minutes. After being stirred for 2 hours at room temperature, the solution is filtered, the precipitate is washed with anhydrous ether, the filtrate is dried over sodium sulfate and the solvents are removed under vacuum. The product is distilled:

B.p.=72°–75° C. at 15 mm of mercury.

m=4.2 g

C) SR 46559 A is then prepared as described in example 1.

EXAMPLE 3

3-(2-diethylamino-2-methyl-propyl)amino-6-(2-chlorophenyl)-5-propyl-pyridazine sesquifumarate. SR 47863 A.

1.7 g of 3-chloro 6-(2-chloro-phenyl) 5-propyl pyridazine and 6 ml of 2-diethylamino 2-methyl propylamine are heated at 110° C. under nitrogen for 20 hours.

After evaporation under vacuum, the mixture is taken up in dichloromethane and washed with a solution of sodium bicarbonate. The organic phase is decanted, dried over magnesium sulfate, filtered and concentrated under vacuum. The residue is chromatographed on silica gel, eluant: dichloromethane/methanol 98/2.

The concentration of the pure fractions gives an oil which is dissolved in 10 ml of methanol. Fumaric acid is added, the methanol is evaporated under vacuum and the sesquifumarate crystallizes from ether.

m=1.6 g

M.p.=144° C.

EXAMPLE 4

3-(2-diethylamino-2-methyl-propyl)amino-6-(2-methoxy-phenyl)-5-methyl-pyridazine.

1.6 g of 3-chloro-6-(2-methoxy-phenyl)-5-methyl pyridazine, 4 g of 2-diethylamino-2-methyl-propylamine and 0.36 g. of ammonium chloride are melted together at 120° C. and the reaction mixture is left at this temperature for 24 hours.

The mixture is cooled to room temperature, extracted with ethyl acetate and washed with a saturated aqueous solution of sodium chloride.

The organic phase is separated, dried over $MgSO_4$, filtered and evaporated to dryness in a vacuum.

The residue is chromatographed on alumina, eluent: ethyl acetate +2% of triethylamine.

The concentration of the pure fractions gives the expected product. The structure is confirmed by NMR spectral analysis.

EXAMPLE 5

3-(2-diethylamino-2-methyl-propyl)amino-5-methyl-6-(2-hydroxyphenyl)-pyridazine. SR 96376.

1 g of the product obtained previously in example 4 is dissolved in 50 ml of 48% hydrobromic acid and the mixture is heated at reflux for 48 hours. After this time, the reaction mixture is evaporated to dryness under vacuum, the residue is made alkaline with an aqueous solution of potassium carbonate and the solution is extracted with dichloromethane. The organic phase is decanted, dried over $MgSO_4$, filtered and evaporated to dryness under vacuum.

The residue is chromatographed on alumina, eluent: ethyl acetate/methanol 9/1+2% of triethylamine.

The concentration of the pure fractions gives a residue which is crystallized from isopropanol.

m=200 mg

M.p.=159.2° C.

EXAMPLES 6 TO 35

A) By using the procedure indicated in example 1A, but by varying the starting ketone, the 6-chloro-pyridazines assembled in the tables 1 and 2 are obtained.

TABLE 1

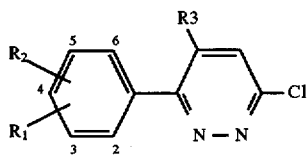

| R₁ | R₂ | R₃ | Physical constants |
|---|---|---|---|
| H | H | —CH₂CH₂CH₃ | M.p.: 52–53° C. |
| Cl(4) | H | —CH₃ | M.p.: 178–180° C. |
| Cl(4) | H | —CH₂CH₂CH₃ | M.p.: 95° C. |
| OCH₃(4) | H | —CH₂CH₂CH₃ | M.p.: 68–69° C. |
| H | H | CH₃ | M.p.: 123–124° C. |
| H | H | phenyl | M.p.: 115° C. |
| H | H | cyclopropyl | M.p.: 119° C. |
| F(4) | H | isopropyl | M.p.: 89–90° C. |
| Cl(2) | H | CH₂CH₂CH₃ | oil, NMR* |
| OCH₃(2) | H | CH₃ | NMR* |
| H | H | benzyl | M.p.: 92° C. |
| Cl(4) | H | Cl-4 phenyl | M.p.: 118–119° C. |
| H | H | Cl-4 phenyl | M.p.: 130° C. |
| Cl(4) | H | phenyl | M.p.: 125° C. |
| Cl(2) | Cl(4) | CH₂CH₂CH₃ | M.p.: 71–72° C. |
| Cl(3) | H | CH₂CH₂CH₃ | M.p.: 48° C. |
| CH₃(4) | H | Cl-4 phenyl | M.p.: 140° C. |
| OCH₃(2) | H | CH₂CH₂CH₃ | oil, NMR* |
| OCH₃(3) | H | CH₂CH₂CH₃ | oil, NMR* |
| F(4) | H | Cl-4 phenyl | M.p. 139° C. |

*NMR: NMR spectral analysis enables the structure of the above compounds to be confirmed.

TABLE 2

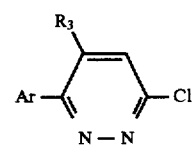

| Ar | R3 | Physical constants |
|---|---|---|
| 2-thienyl | phenyl | M.p: 148° C. |
| 2-Cl 5-thienyl | phenyl | NMR |
| 3-pyridyl | phenyl | M.p: 184° C. |
| 2-pyridyl | phenyl | M.p: 138° C. |
| 4-pyridyl | phenyl | M.p: 193° C. |

B) Starting from the chloro derivatives of table 1 and by following the procedure employed in example 1, the compounds according to the invention assembled in table 3 below are obtained by varying the amines NH₂R₄ used.

TABLE 3

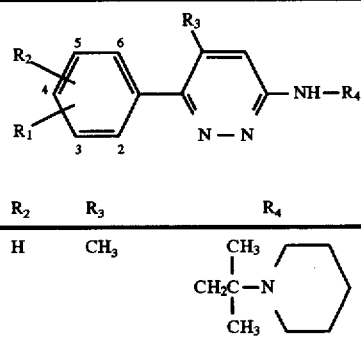

| SR No. Ex. No. | R₁ | R₂ | R₃ | R₄ | salt or base M.p. |
|---|---|---|---|---|---|
| 46729A 6 | Cl(4) | H | CH₃ | CH₃—CH₂C—N(piperidine)—CH₃ | dihydrochloride 240–242° C. |
| 46732A 7 | H | H | nC₃H₇ | " | sesquifumarate 159–161° C. |
| 46733A 8 | Cl(4) | H | CH₃ | CH₂—C(CH₃)(CH₃)—N(C₂H₅)(C₂H₅) | Fumarate 138–140° C. |
| 47020A 9 | H | H | CH₃ | " | sesquifumarate 161° C. |
| 47047A 10 | H | H | phenyl | " | fumarate 193° C. |
| 47054A 11 | Cl(4) | H | nC₃H₇ | " | sesquifumarate 152–154° C. |
| 47068 12 | OCH₃(4) | H | nC₃H₇ | " | 65–66° C. base |

TABLE 3-continued

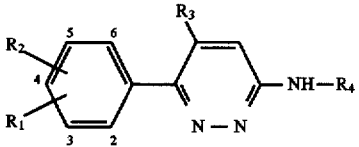

| SR No. Ex. No. | $R_1$ | $R_2$ | $R_3$ | $R_4$ | salt or base M.p. |
|---|---|---|---|---|---|
| 47069A 13 | OH(4) | H | $nC_3H_7$ | " | hydrobromide 179–181° C. |
| 47097A 14 | H | H | cyclopropyl | " | sesquifumarate 158–160° C. |
| 47098A 15 | F(4) | H | iPr | " | sesquifumarate hemihydrate 143–145° C. |
| 47138A 16 | H | H | $nC_3H_7$ | $CH_2-\underset{\underset{CH_3}{\vert}}{\overset{\overset{CH_3}{\vert}}{C}}-N\diagup\!\!\diagdown O$ | sesquifumarate 149–151° C. |
| 47153A 17 | H | H | phenyl | $CH_2-\underset{\underset{CH3}{\vert}}{\overset{\overset{CH_3}{\vert}}{C}}-CH_2-N\diagup^{CH_3}\diagdown_{CH_3}$ | 164° C. sesquifumarate |
| 47227A 18 | H | H | benzyl | $CH_2-\underset{\underset{CH_3}{\vert}}{\overset{\overset{CH_3}{\vert}}{C}}-N\diagup^{C_2H_5}\diagdown_{C_2H_5}$ | fumarate 163° C. |
| 47297A 19 | Cl(4) | H | Cl-4 phenyl | " | dihydrochloride 138° C. hydrate |
| 47608A 20 | H | H | Cl-4 phenyl | " | dihydrochloride 147° C. |
| 47609A 21 | Cl(4) | H | phenyl | " | dihydrochloride 147° C. |
| 47655A 22 | Cl(2) | Cl-(4) | $nC_3H_7$ | " | sesquifumarate 165–166° C. |
| 47673 23 | H | H | $nC_3H_7$ | $CH_2-\underset{\underset{C_2H_5}{\vert}}{\overset{\overset{C_2H_5}{\vert}}{C}}-N\diagup^{CH_3}\diagdown_{CH_3}$ | base oil NMR* |
| 47878A 24 | Cl(3) | H | $nC_3H_7$ | $CH_2-\underset{\underset{CH_3}{\vert}}{\overset{\overset{CH_3}{\vert}}{C}}-N\diagup^{C_2H_5}\diagdown_{C_2H_5}$ | sesquifumarate 146° C. |
| 47890A 25 | $CH_3(4)$ | H | Cl-4 phenyl | " | dihydrochloride 138° C. |
| 47967 26 | F(4) | H | Cl-4 phenyl | " | 98° C. base |
| 48079A 27 | $OCH_3(2)$ | H | $nC_3H_7$ | " | sesquifumarate 95° C. |
| 48080 28 | OH(2) | H | $nC_3H_7$ | " | 159.5° C. base |
| 48081A 29 | $OCH_3(3)$ | H | $nC_3H_7$ | " | dihydrochloride NMR |
| 48082 30 | OH(3) | H | $nC_3H_7$ | " | 166° C. base |

NMR spectrum of SR 47673

(DMSO d$_6$; 200 MHz) 0.70 (t: 3 H); 0.80 (t; 6H); 1.30 (q; 2H); 1.50 (m; 4H); 2.30 (s; 6H); 2.40 (m; 2H); 3.40 (m; 2H); 6.20 (m; 1H); 6.80 (s; 1H); 7.35 (s; 5H).

NMR spectrum of SR 48081 A (DMSO d$_6$; 200 MHz) 0.80 (t; 3H); 1.40 (m; 8H); 1.5 (s; 6H); 2.56 (q; 2H); 3.40 (b.s.; 4H); 3.80 (s; 3H); 4.00 (d; 2H); 7.02 (m; 3H); 7.40 (t; 1H); 7.83 (b.s.; 1H).

The following abbreviations are used for the analysis of a NMR spectrum.

s=singlet; b.s.: broad singlet; d: doublet; t: triplet; q: quadruplet; m: multiplet.

C) Starting from the chloro derivatives of table 2 and by following the procedure described in example 1, the compounds according to the invention assembled in table 4 below are obtained by varying the amines NH$_2$R$_4$ used.

TABLE 4

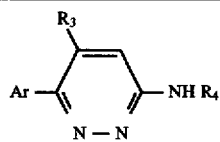

| SR No. Ex. No. | Ar | R3 | R4 | Salt or base |
|---|---|---|---|---|
| 47674A 31 | 2-thienyl | phenyl | CH3<br>\|<br>CH2—C—N⟨C2H5/C2H5<br>\|<br>CH3 | dihydro-chloride 133° C. |
| 47675A 32 | 5-Cl 2-thienyl | phenyl | " | dihydro-chloride 130° C. decomposition |
| 47802A 33 | 3-pyridyl | phenyl | " | trihydro-chloride 225° C. |
| 47803A 34 | 2-pyridyl | phenyl | " | trihydro-chloride 233° C. |
| 47804A 35 | 4-pyridyl | phenyl | " | trihydro-chloride 239° C. |

The compounds according to the invention were studied with respect to their pharmacological properties and in particular with respect to their affinity for the muscarinic cholinergic receptors of type M$_1$ and M$_2$.

In vitro, the compounds (I) were assayed according to the technique described by Watson J. D. et al. (Life Sciences, 1982, 31, 2019–2029) as far as their affinity for the receptors of type M$_1$ is concerned and according to the technique described by Hammer R. et al. (Nature, 1980, 283, 90–92) and Hulme E. C. et al. (Molecular Pharmacology, 1978, 14, 737–750) as far as their affinity for the receptors of the M$_2$ type is concerned.

The compounds according to the invention exhibit good affinity for the receptors of type M$_1$ and a marked specificity for the central receptors of type M$_1$ as opposed to receptors of type M$_2$.

As an example, the compound SR 46559 A showed an inhibiting concentration 50 expressed in micromoles of 0.11 and 2.2, respectively, on the M$_1$ and M$_2$ receptors.

Similarly, the compound SR 47047 A showed inhibiting concentrations 50 of 0.04 and 0.9, respectively, on the M$_1$ and M$_2$ receptors.

In vivo, the compounds according to the invention were assayed for their effect on the rotations induced by intrastriatal pirenzepine in the test described by Worms P. et al. (Psychopharmacology, 1987, 93, 489–493) modified in that the administration of the compounds by the oral route took place 4 hours before, instead of 30 minutes before, the injection of pirenzepine.

At a dose of 3 mg per kg of body weight, the compounds according to the invention strongly inhibit the number of rotations induced by pirenzepine. Thus, as an example, the compound SR 46559 A inhibits the rotations induced by pirenzepine by 78%.

Furthermore, the compounds according to the invention were shown to be active in the passive avoidance tests in the rat described by Jarvik M. E. et el. in Psychol. Med., 1967, 21, 221–224 and by Worms P. et al. in Psychopharmacol., 1989, 98, 286–288.

Thus, according to the results of these tests, the compounds according to the invention counteract the amnesia induced by scopolamine administered by the intraperitoneal route at 0.5 mg/kg and the amnesia induced by pirenzepine administered intraperitoneally at 75 mg/kg. For example, SR 46559 A exhibits an oral efficient dose 50 of 0.25 mg/kg and 0.027 mg/kg, respectively, in each of these tests.

Moreover, some compounds according to the invention were studied in several predictive models of antidepressant activity such as the forced swimming test described by Porsolt et al. (Arch. Intern. Pharmacodyn., 1977, 229, 327–336) and the test of antagonism of reserpine-induced ptosis described by Gouret et al. (J. Pharmacol. (Paris), 1977, 8, 333–350). SR 46559 A in particular was shown to be inactive in these tests at oral doses varying from 0.1 to 10 mg/kg.

Finally, the compounds according to the invention did not show any sign of toxicity at the doses at which they are active.

Consequently, the compounds (I) may be used as medicines.

The results indicated show that the compounds according to the invention exhibit good affinity for the muscarinic receptors and good activity in the tests of amnesia induced by scopolamine or pirenzepine. They allow the use of the products according to the invention to be contemplated in all cases in which a cholinergic deficit is indicated and particularly for the treatment of cognitive and memory disorders, and degenerative syndromes associated with senescence and senile dementia.

In accordance with another of its features, the present application thus relates to pharmaceutical compositions containing at least one of the compounds of formula (I) or one of their salts as active ingredient.

In the pharmaceutical compositions of the present invention for oral, sublingual, transdermal or rectal administration, the active ingredients of formula I above may be administered in specific forms of administration, in combination with the standard pharmaceutical vehicles, to humans especially for the treatment of cognitive or memory disorders or degenerative syndromes. The appropriate specific forms of administration comprise the forms used for the oral route such as tablets, capsules, powders, granules and solutions or oral suspensions, the forms used for sublingual and buccal administration, the forms for subcutaneous, intramuscular or intravenous administration and the forms for rectal administration.

In order to obtain the desired effect, the dose of the active ingredient may vary between 0.5 and 500 mg per day.

Each unit dose may contain from 0.1 to 100 mg of active ingredient in combination with a pharmaceutical vehicle. This unit dose may be administered 1 to 5 times per day.

When a solid composition is prepared in the form of tablets, the principal active ingredient is mixed with a pharmaceutical vehicle such as gelatine, starch, lactose, magnesium stearate, talc, gum arabic, or similar substances. The tablets may be coated with sucrose or other suitable materials or they may be treated so that they have sustained or delayed activity and so that they release continuously a predetermined amount of active ingredient.

A preparation of capsules is obtained by mixing the active ingredient with a diluent and by pouring the mixture obtained into soft or hard capsules.

The powders or granules dispersible in water may contain the active ingredient mixed with dispersing agents or wetting agents or suspending agents such as polyvinylpyrrolidone, as well as with sweeteners or taste modifiers.

In the case of rectal administration, suppositories are used which are prepared with binders melting at the rectal temperature, for example cocoa butter or polyethylene glycols.

For parenteral administration, aqueous suspensions, isotonic saline solutions or sterile and injectable solutions which contain pharmacologically compatible wetting and/or dispersing agents, for example propylene glycol or butylene glycol, are used.

The active ingredient may also be formulated in the form of microcapsules, with or without one or more additives or supports.

As an example of a galenic preparation, capsules may be prepared containing:

|  |  |
| --- | --- |
| SR 46559 A | 0.010 g |
| Lactose | 0.050 g |
| Magnesium stearate | 0.005 g | by mixing the above ingredients intimately and pouring the mixture into gelules of hard gelatine.

In a large number of cases, these are substances which are active on the cardiovascular system and have in particular a hypotensive or vasodilative effect; in other cases, an anti-inflammatory and analgesic action has been mentioned for pyridazine derivatives.

French patents 2 141 697, 2 510 997 and 2 510 998 disclose pyridazine derivatives which are variously substituted on the pyridazine ring and all carry, in the 3-position, an amino substituent of the type

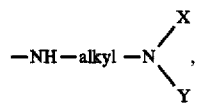

in which X and Y independently are hydrogen or an alkyl group or form, with the nitrogen atom to which they are bonded, a heterocycle such as morpholine.

All these compounds are active on the central nervous system as antidepressants.

According to a second aspect of the present invention, it has now been found that by modifying the nature and/or position of the substituents on the pyridazine ring, compounds are obtained which have lost their antidepressant activity and acquired a valuable activity as $M_1$-type muscarinic cholinergic ligands.

According to a first feature of this aspect, the present invention relates to novel pyridazine derivatives of the general formula

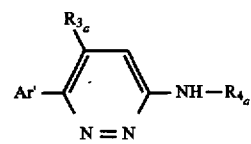

(IA)

in which

Ar' is a group

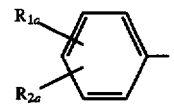

a pyridyl or a thienyl;

$R_{1a}$ and $R_{2a}$ independently are each hydrogen, a halogen atom, a hydroxyl group, a trifluoromethyl group, a $C_1-C_4$ alkoxy group or a $C_1-C_4$ alkyl group;

$R_{3a}$ is a $C_1-C_4$ alkyl group or a phenyl; and $R_{4a}$ is:

a group

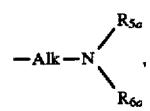

in which Alk is a $C_1-C_6$ alkylene group, $R_{5a}$ is hydrogen or a $C_1-C_6$ alkyl group and $R_{6a}$ is a $C_1-C_4$ alkyl group, a benzyl or a $C_3-C_7$ cycloalkyl, or $R_{5a}$ and $R_{6a}$ form, with the nitrogen atom to which they are bonded, a heterocycle selected from morpholine, thiomorpholine, pyrrolidine, N-methylpiperazine and piperidine which is unsubstituted or substituted by one or more methyl groups, by a hydroxyl, by a phenyl or by a benzyl;

a group

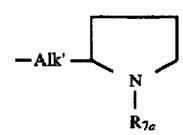

in which Alk' is a $C_1-C_3$ alkylene group and $R_{7a}$ is a $C_1-C_4$ alkyl group; or a group

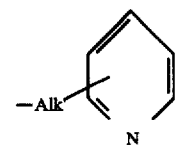

in which Alk' is as defined above and substitutes the pyridine in the 2-, 3- or 4-position, with the limitation that $R_{1a}$ and $R_{2a}$ are not simultaneously hydrogen when $R_{4a}$ is a group $(CH_2)_2NR_{5a}R_{6a}$, and to the salts of the compounds of formula (I) with mineral or organic acids.

The compounds (I) according to the invention in which Ar' is a group

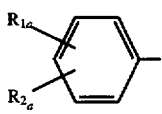

are preferred.

Among these, particularly preferred compounds are those in which $R_{4a}$ is one of the following groups:

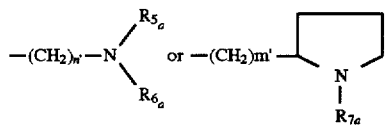

in which $R_{5a}$ $R_{6a}$ and $R_{7a}$ are as defined above for (I), n' is between 1 and 6, and preferably equal to 2, 3 or 4 and m' is between 1 and 3, preferably equal to 1 or 2.

When the compound (I) has an asymmetric carbon, the 2 stereoisomers form part of the invention.

According to a second feature, the present invention relates to a method of preparing the compounds of formula (IA) which is represented by the following reaction scheme:

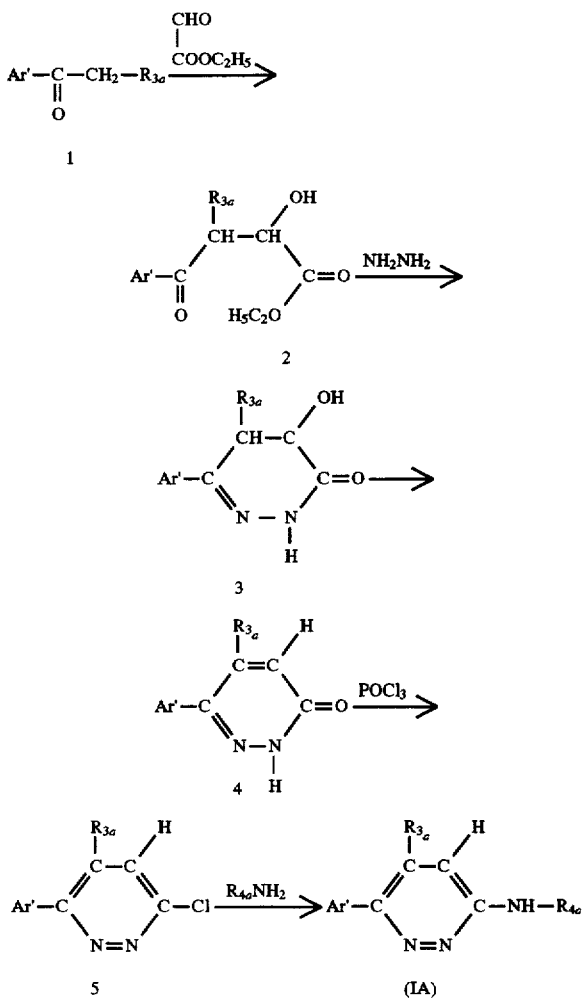

Heating the ketone 1 with ethyl glyoxylate at a temperature of between 80° and 140° C. gives the hydroxyketoester 2. The crude reaction mixture is then taken up in an inert solvent such as n-butanol, and hydrazine hydrate is added.

Refluxing for 24 hours gives the hydroxypyridazinone 3, which, when heated in an acid medium, yields the 2H-pyridazin-3-one 4 by dehydration.

Heating the latter with excess phosphorus oxychloride gives the 3-chloropyridazine 5. The reaction is carried out without a solvent or in the presence of an inert solvent such as acetonitrile.

Finally, heating the chlorine derivative 5 with a large excess of amine $R_{4a}NH_2$ at a temperature of between 100° and 150° C., in the presence of a small amount of ammonium chloride, yields the compound (IA). The reaction is carried out without a solvent or in an inert solvent such as n-butanol. The product (IA) is isolated by extraction and purified by chromatography.

If desired, the resulting base can be converted to a salt by a known method and especially by reaction with an equimolecular amount of acid in a suitable solvent.

The compounds (IA) in which Ar' is a hydroxyphenyl or dihydroxyphenyl group are prepared from the corresponding compounds (IA) in which Ar' is a methoxyphenyl or dimethoxyphenyl group by demethylation in an acid medium.

The following Examples illustrate the preparation of compounds of formula (IA) without implying a limitation.

EXAMPLE 1A

3-[(N-Ethylpyrrolidin-2-yl)methylamino]-5-methyl-6-phenylpyridazine (SR 96185)

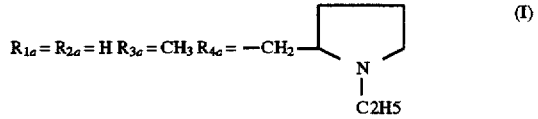

A) 3-Chloro-5-methyl-6-phenylpyridazine

1. Ethyl 2-hydroxy-3-methyl-4-phenyl-4-oxobutyrate

A mixture of 13.4 g of propiophenone and 15.3 g of ethyl glyoxylate is heated at 135° C. for 5 hours.

The resulting product is used as such for the next operation.

2. 5-Methyl-6-phenyl-2H-pyridazin-3-one

The crude product obtained above is dissolved in 150 ml of n-butanol, 9.44 ml of hydrazine hydrate are then added and the mixture is refluxed for 24 hours.

Part of the n-butanol is distilled at ordinary pressure in order to remove the water formed in the reaction as an azeotrope. The mixture is then concentrated to dryness under vacuum. The residue is taken up in a mixture of 100 ml of acetic acid and 10 ml of concentrated hydrochloric acid. The mixture is heated at 100° C. for 4 hours. The solution is poured into cold water and left to crystallize.

The solid is filtered off and dried.

Weight: 11.6 g M.p.: 218° C.

3. 3-Chloro-5-methyl-6-phenylpyridazine 50 ml of phosphorus oxychloride are added to 12 g of the pyridazinone obtained above and the mixture is heated at 80° C. for 4 hours.

The mixture is poured slowly on to ice and rendered alkaline with a 20% solution of sodium hydroxide.

The precipitate is filtered off, washed copiously with water and recrystallized from isopropanol.

9.9 g of the expected product are obtained.

M.p.: 122° C.

B) SR 96185

A mixture of 2 g of the chlorine derivative obtained above, 5 g of 2-aminomethyl-1-ethylpyrrolidine and 0.5 g of ammonium chloride is heated at 130° C. for 3 hours under an inert atmosphere. The reaction mixture is poured into water and extracted with ethyl acetate. The solution is dried and the solvent is evaporated off to dryness. The residue is chromatographed on a silica column. Elution with an ethyl acetate/methanol mixture (95/5 vol/vol) gives an oil, which crystallizes from a small quantity of ethyl acetate.

Weight: 2 g M.p.: 92° C.

EXAMPLE 2

3-(2-Diethylaminoethylamino)-5-methyl-6-(4-methoxyphenyl)pyridazine dioxalate (SR 96194 A)

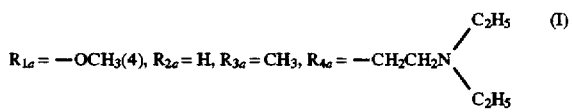

$R_{1a} = -OCH_3(4)$, $R_{2a} = H$, $R_{3a} = CH_3$, $R_{4a} = -CH_2CH_2N(C_2H_5)_2$   (I)

A) 3-Chloro-5-methyl-6-(4-methoxyphenyl)pyridazine

1. Ethyl 2-hydroxy-3-methyl-4-(4-methoxyphenyl)-4-oxobutyrate

A mixture of 82 g of 4-methoxypropiophenone and 76.6 g of ethyl glyoxylate is heated at 135° C. for 15 hours.

The resulting product is used as such for the next operation.

2. 5-Methyl-6-(4-methoxyphenyl)-2H-pyridazin-3-one

The crude product obtained above is dissolved in 250 ml of n-butanol, 38 g of hydrazine hydrate are then added and the mixture is refluxed for 24 hours.

Part of the n-butanol is distilled at ordinary pressure in order to remove the water formed in the reaction as an azeotrope. The mixture is then concentrated to dryness under vacuum. The residue is taken up in a mixture of 450 ml of acetic acid and 50 ml of concentrated hydrochloric acid. The mixture is heated at 100° C. for 4 hours. The solution is poured into cold water and left to crystallize.

The solid is filtered off and dried.

Weight: 40 g M.p.: 216° C.

3. 3-Chloro-5-methyl-6-(4-methoxyphenyl)pyridazine 250 ml of phosphorus oxychloride are added to 10 g of the pyridazinone obtained above and the mixture is heated at 80° C. for 10 hours.

The mixture is poured slowly on to ice and rendered alkaline with a 20% solution of sodium hydroxide.

The precipitate is filtered off, washed copiously with water and recrystallized from methanol.

9 g of the expected product are obtained.

M.p.: 132° C.

B) SR 98194 A

A mixture of 2.3 g of the chlorine derivative obtained above, 5 g of N,N-diethylethylenediamine and 0.5 g of ammonium chloride is heated at 135° C. for 4 hours under an inert atmosphere. The reaction mixture is poured into water and extracted with ethyl acetate. The solution is dried and the solvent is evaporated off to dryness.

Weight: 2.3 g.

Dioxalate

The above base is dissolved in hot isopropanol, and a solution of 2.2 equivalents of oxalic acid in the minimum quantity of boiling isopropanol is added. The dioxalate precipitates on cooling. It is filtered off and recrystallized from absolute ethanol.

M.p.: 136° C.

EXAMPLES 3A TO 80A

A) The 3-chloropyridazines collated in Tables 1 and 2 below are obtained by following the procedure indicated in Example 1A, but varying the starting ketone:

TABLE 1A

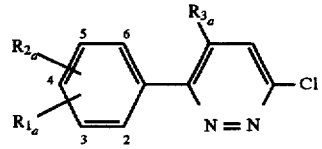

| $R_{1_a}$ | $R_{2_a}$ | $R_{3_a}$ | Physical constants |
|---|---|---|---|
| Cl(4) | H | $CH_3$ | M.p.: 178–180° C. |
| Cl(4) | H | $CH_2CH_3$ | M.p.: 86° C. |
| Cl(2) | Cl(4) | $CH_3$ | M.p.: 116° C. |
| Cl(3) | H | $CH_3$ | M.p.: 95° C. |
| $CF_3(3)$ | H | $CH_3$ | M.p.: 120° C. |
| F(4) | H | $CH_3$ | M.p.: 153° C. |
| $CH_3(4)$ | H | $CH_3$ | M.p.: 165–166° C. |
| Cl(4) | H | $CH_2CH_2CH_3$ | M.p.: 95° C. |
| $OCH_3(4)$ | H | $CH_2CH_2CH_3$ | M.p.: 68–69° C. |
| H | H | $CH_3$ | M.p.: 123–124° C. |
| H | H | phenyl | M.p.: 115° C. |
| Cl(3) | Cl(5) | $CH_3$ | M.p.: 104° C. |
| Cl(3) | Cl(4) | $CH_3$ | M.p.: 167° C. |
| H | H | $CH_2CH_2CH_3$ | M.p.: 60° C. |
| $OCH_3(2)$ | H | $CH_3$ | M.p.: 74° C. |

TABLE 2A

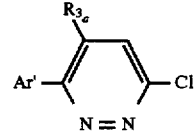

| Ar' | $R_{3a}$ | Physical constants |
|---|---|---|
| Pyrid-2-yl | $CH_3$ | 135° C. |
| Pyrid-3-yl | $CH_3$ | 142° C. |
| Thien-2-yl | $CH_3$ | 99° C. |

B) The compounds (I) collated in Tables 3 and 4 are obtained from the chlorine derivatives of Examples 1A, 2A and 3A by following the technique of Example 1B, varying the amines used. These compounds are characterized by their melting point (M.p.) or their optical rotation $[\alpha]_D$.

TABLE 3 A

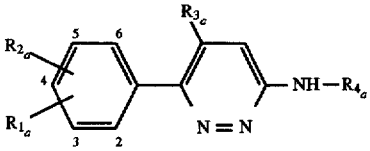

| Ex. n° | SR ref. n° | $R_{1_a}$ | $R_{2_a}$ | $R_{3_a}$ | $R_{4_a}$ | Salt or base M.p. or $[\alpha]_D$ |
|---|---|---|---|---|---|---|
| 3A | 96181 | H | H | $(CH_2)_2-CH_3$ | 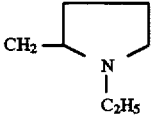 | Base 94° C. |
| 4A | 96198 | Cl(4) | H | $CH_3$ | " | Base 90° C. |
| 5A | 96222 | Cl(2) | Cl(4) | $CH_3$ | " | Base 113° C. |
| 6A | 46004A | $CF_3(3)$ | H | $CH_3$ | " | Dihydrochloride 0.5$H_2O$ 180° C. (decomposition) |
| 7A | 96204A | H | H | $CH_3$ | 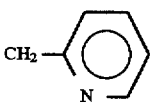 | Dihydrochloride 221° C. |
| 8A | 96240A | Cl(4) | H | $CH_3$ | " | Dihydrochloride 222–223° C. |
| 9A | 46005A | Cl(3) | H | $CH_3$ | " | Hydrochloride 1$H_2O$ 182° C. |
| 10A | 45991A | Cl(4) | H | $CH_2CH_3$ | " | Dihydrochloride 215–217° C. |
| 11A | 96220A | H | H | $CH_3$ | 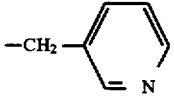 | Dihydrochloride 1$H_2O$ 189° C. |
| 12A | 96205A | H | H | $CH_3$ | 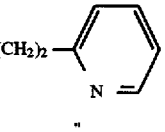 | Dihydrochloride 1$H_2O$ 133° C. |
| 13A | 96239A | Cl(4) | H | $CH_3$ | " | Dihydrochloride 224° C. |
| 14A | 46035A | Cl(3) | H | $CH_3$ | 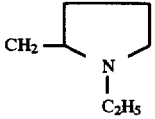 | Dihydrochloride 1$H_2O$ 172° C. |
| 15A | 46079A | Cl(4) | H | $CH_2CH_3$ | " | Fumarate 163–165° C. |
| 16A | 96193A | $OCH_3(4)$ | H | $CH_3$ | 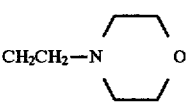 | Dihydrochloride 219° C. |
| 17A | 96197A | Cl(4) | H | $CH_3$ | " | Dihydrochloride 0.5$H_2O$ 247° C. |
| 18A | 96223A | Cl(2) | Cl(4) | $CH_3$ | " | Dihydrochloride 250° C. (decomposition) |
| 19A | 45964A | $CF_3(3)$ | H | $CH_3$ | " | Dihdyro- |

TABLE 3 A-continued

| Ex. n° | SR ref. n° | $R_{1a}$ | $R_{2a}$ | $R_{3a}$ | $R_{4a}$ | Salt or base M.p. or $[\alpha]_D$ |
|---|---|---|---|---|---|---|
| | | | | | | chloride 2H$_2$O 183° C. |
| 20A | 45944A | Cl(3) | H | CH$_3$ | " | Dihydrochloride 1.5H$_2$O 212° C. |
| 21A | 46179A | Cl(3) | Cl(5) | CH$_3$ | " | Dihydrochloride 1H$_2$O 198° C. |
| 22A | 46197A | Cl(4) | H | CH$_2$CH$_3$ | CH$_2$CH$_2$—N(morpholino) | Difumarate 168–170° C. |
| 23A | 46222A | F(4) | H | CH$_3$ | " | Dihydrochloride 217–219° C. |
| 24A | 46223A | CH$_3$(4) | H | CH$_3$ | " | Fumarate 165–167° C. |
| 25A | 46224A | Cl(3) | Cl(4) | CH$_3$ | " | Dihydrochloride 228–230° C. |
| 26A | 46405A | Cl(4) | H | CH$_3$ | CH$_2$—CH$_2$—N(iPr)$_2$ | Dihydrochloride 1H$_2$O 157–160° C. |
| 27A | 46534A | Cl(4) | H | n.C$_3$H$_7$ | " | Fumarate 0.5H$_2$O 130° C. |
| 28A | 46431A | Cl(4) | H | CH$_3$ | CH$_2$—CH$_2$—N(4-hydroxypiperidino) | Dihydrochloride 226–228° C. |
| 29A | 46432A | Cl(4) | H | CH$_3$ | CH$_2$—CH$_2$—N(pyrrolidino) | Dihydrochloride 0.5H$_2$O 208–210° C. |
| 30A | 46514A | Cl(4) | H | CH$_3$ | CH$_2$—CH$_2$—N(piperidino) | Dihydrochloride 0.5H$_2$O 172–174° C. |
| 31A | 46637A | Cl(4) | H | n.C$_3$H$_7$ | " | Dihydrochloride 1H$_2$O 205° C. |
| 32A | 46636A | H | H | n.C$_3$H$_7$ | " | Dihydrochloride 1H$_2$O 207° C. |
| 33A | 96224A | Cl(4) | H | CH$_3$ | CH$_2$CH$_2$—N(C$_2$H$_5$)$_2$ | Dioxalate 131° C. |
| 34A | 96230A | Cl(2) | Cl(4) | CH$_3$ | " | Dioxalate 1H$_2$O 106° C. |
| 35A | 96194A | OCH$_3$(4) | H | CH$_3$ | " | Dioxalate 136° C. |
| 36A | 96266A | Cl(3) | H | CH$_3$ | " | Dioxalate 136° C. |

TABLE 3 A-continued

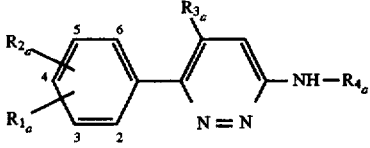

| Ex. n° | SR ref. n° | $R_{1_a}$ | $R_{2_a}$ | $R_{3_a}$ | $R_{4_a}$ | Salt or base M.p. or $[\alpha]_D$ |
|---|---|---|---|---|---|---|
| 37A | 96232A | Cl(4) | H | $CH_3$ | $CH_2CH_2N(CH_3)_2$ | Dihyrdochloride 258–259° C. |
| 38A | 46010A | Cl(4) | H | $CH_2CH_3$ | " | Dihydrochloride 0.3$H_2O$ 223–225° C. |
| 39A | 46081A | F(4) | H | $CH_3$ | " | Dihydrochloride 0.25$H_2O$ 233–235° C. |
| 40A | 46082A | $CH_3$(4) | H | $CH_3$ | " | Dihydrochloride 235–237° C. |
| 41A | 45960A | Cl(4) | H | $CH_3$ | $(CH_2)_3-N(CH_3)_2$ | Dihydrochloride 256–258° C. |
| 42A | 46080A | Cl(4) | H | $CH_2CH_3$ | " | Dihydrochloride 0.6$H_2O$ 202° C. |
| 43A | 46731A | Cl(4) | H | $CH_3$ | $CH_2-CH_2-N$(2,2,6,6-tetramethylpiperidinyl) | Fumarate 213–215° C. |
| 44A | 46730A | H | H | $n.C_3H_7$ | " | 2.5 Fumarate 193–195° C. |
| 45A | 96231A | Cl(4) | H | $CH_3$ | $CH_2CH_2NH-CH_3$ | Oxalate 1$H_2O$ 111–113° C. |
| 46A | 45961A | Cl(4) | H | $CH_3$ | $(CH_2)_3-N$(morpholino) | Dihydrochloride 250–252° C. |
| 47A | 45988A | Cl(4) | H | $CH_3$ | $(CH_2)_4-N(CH_3)_2$ | Dihydrochloride 244–246° C. |
| 48A | 45989A | Cl(4) | H | $CH_2CH_3$ | " | Dihydrochloride 2$H_2O$ 214–216° C. |
| 49A | 46377A | H | H | $n.C_3H_7$ | $(CH_2)_2NCH_2C_6H_5$ \| iPr | Dihydrochloride 0.5$H_2O$ 182–184° C. |

TABLE 3 A-continued

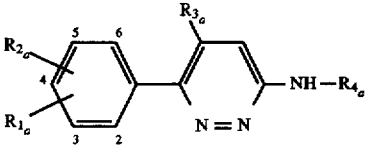

| Ex. n° | SR ref. n° | $R_{1_a}$ | $R_{2_a}$ | $R_{3_a}$ | $R_{4_a}$ | Salt or base M.p. or $[\alpha]_D$ |
|---|---|---|---|---|---|---|
| 50A | 46532A | H | H | n.C$_3$H$_7$ | CH$_2$—CH$_2$—N(CH$_3$)(cyclohexyl) | Fumarate 1H$_2$O 152° C. |
| 51A | 46728A | Cl(4) | H | CH$_3$ | (CH$_2$)$_2$—N-piperidinyl-CH$_2$C$_6$H$_5$ | Dihydro-chloride 0.5H$_2$O 224–226° C. |
| 52A | 96290A | H | H | CH$_3$ | CH$_2$—CH$_2$—N(thiomorpholine) | Dioxalate 181° C. |
| 53A | 96291 | H | H | CH$_3$ | (CH$_2$)$_2$—N(piperazine)N—CH$_3$ | Base 98° C. |
| 54A | 46352A | H | H | n.C$_3$H$_7$ | CH$_2$—CH$_2$—N(iPr)$_2$ | Fumarate 156–157° C. |
| 55A | 46359A | H | H | " | (CH$_2$)$_2$—N(CH$_2$CH$_3$)((CH$_2$)$_3$CH$_3$) | Fumarate 113–114° C. |
| 56A | 46378A | H | H | " | (CH$_2$)$_2$N(nBu)$_2$ | Fumarate 95–96° C. |
| 57A | 46533A | H | H | " | (CH$_2$)$_2$—N(nPr)$_2$ | Fumarate 109–110° C. |
| 58A | 46180 | Cl(3) | Cl(5) | CH$_3$ | CH$_2$-pyrrolidinyl-N-C$_2$H$_5$ | Dihydro-chloride 192° C. |
| 59A | 46195 | Cl(4) | H | C$_2$H$_5$ | CH$_2$-(4-pyridyl) | Fumarate 180–182° C. |
| 60A | 46196 | CH$_3$(4) | H | CH$_3$ | CH$_2$-pyrrolidinyl-N-C$_2$H$_5$ | Base 106° C. |
| 61A | 96268 | Cl(4) | H | CH$_3$ | (+) CH$_2$-pyrrolidinyl-N-C$_2$H$_5$ | Yellow oil $\alpha^{19}$ = +65° (2% CHCl$_3$) |

TABLE 3 A-continued

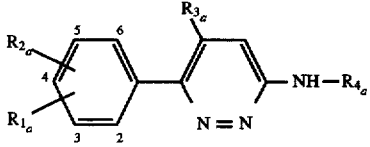

| Ex. n° | SR ref. n° | $R_{1a}$ | $R_{2a}$ | $R_{3a}$ | $R_{4a}$ | Salt or base M.p. or $[\alpha]_D$ |
|---|---|---|---|---|---|---|
| 62A | 96269 | Cl(4) | H | $CH_3$ | 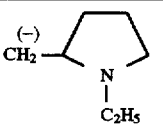 | Yellow oil $\alpha^{19} = -68°$ (2% $CHCl_3$) |
| 63A | 96272 | H | H | $n.C_3H_7$ | 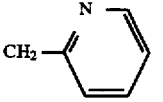 | Dihydrochloride 218° C. |
| 64A | 46433 | H | H | $n.C_3H_7$ | 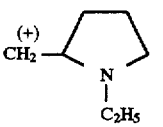 | Base 83° C. $\alpha^{22} = +68.6°$ (C = 1, $CHCl_3$) |
| 65A | 46434 | H | H | $n.C_3H_7$ | 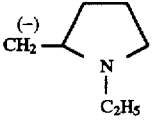 | Base 82° C. $\alpha^{21} = -70°$ (C = 1, $CHCl_3$) |
| 66A | 46430 | F(4) | H | $CH_3$ | 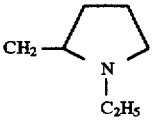 | Dihydrochloride 206° C. |
| 67A | 46514 | Cl(4) | H | $CH_3$ | 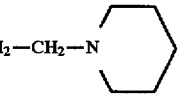 | Dihydrochloride $1H_2O$ 174° C. |
| 68A | 46636 | H | H | $n.C_3H_7$ | 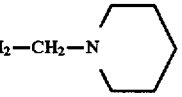 | Dihydrochloride $1H_2O$ 207° C. |
| 69A | 46637 | Cl(4) | H | $n.C_3H_7$ | 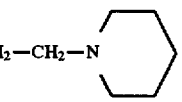 | Dihydrochloride $1H_2O$ 205° C. |
| 70A | 47046 | H | H | $C_6H_5$ | 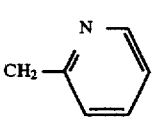 | Hemifumarate 165° C. |
| 71A | 47186 | H | H | $C_6H_5$ | 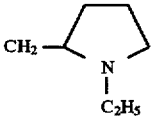 | Fumarate 158° C. |
| 72A | 47226 | H | H | $C_6H_5$ | 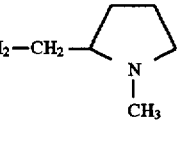 | Sesquifumarate 191° C. |

TABLE 3 A-continued

Structure: Phenyl ring with $R_2$ at position 5, $R_1$ at position 4 (positions 3,2 on lower ring), connected to pyridazine with $R_{3a}$ and NH—$R_{4a}$, N=N

| Ex. n° | SR ref. n° | $R_{1a}$ | $R_{2a}$ | $R_{3a}$ | $R_{4a}$ | Salt or base M.p. or $[\alpha]_D$ |
|---|---|---|---|---|---|---|
| 73A | 96305 | OH(2) | H | $CH_3$ | $CH_2$—pyrrolidinyl-N-$C_2H_5$ | Base 0.3$H_2O$ 160° C. |
| 74A | 96306A | Cl(4) | H | $CH_3$ | $CH_2CH_2N(CH_3)$—cyclohexyl | Dihydrochloride 0.5$H_2O$ 257° C. |
| 75A | 96307A | Cl(4) | H | $CH_3$ | $CH_2CH_2N(H)$—cyclohexyl | Dioxalate 0.5$H_2O$ 179° C. |
| 76A | 96308A | H | H | $CH_3$ | $CH_2CH_2N(H)$—cyclohexyl | Hydrochloride $H_2O$ 196° C. |

TABLE 4A

Structure: Ar'—pyridazine with $R_{3a}$, =NH—Alk—N($R_{5a}$)($R_{6a}$), N=N; or Alk—N($R_{5a}$)($R_{6a}$)

| Ex. | SR ref. n° | Ar' | $R_{3a}$ | | Salt or base M.p. |
|---|---|---|---|---|---|
| 77A | 46457A | Pyrid-2-yl | $CH_3$ | $CH_2$—$CH_2$—$N(iPr)_2$ | Fumarate 145° C. |
| 78A | 46578A | Pyrid-3-yl | $CH_3$ | " | Fumarate 1.5$H_2O$ 175° C. |
| 79A | 46640A | Pyrid-2-yl | $CH_3$ | $CH_2$—$CH_2$—N(piperidinyl) | Difumarate 146° C. |
| 80A | 46641A | Thien-2-yl | $CH_3$ | " | Dihydrochloride 0.5$H_2O$ 265° C. |

The products according to the invention were studied for their pharmacological properties and in particular for their affinity for the muscarinic cholinergic receptors.

In vitro, the compounds (I) were tested according to the technique described by Watson J. D. et al. (Life Science, 1982, 31, 2019–2029) for their activity on the $M_1$-type receptors, and according to the technique described by Hamer R. et al. (Nature, 1980, 283, 90–92) and Hulme E. C. et al. (Molecular Pharmacology, 1978, 14, 737–750) for their activity on the $M_2$-type receptors.

The compounds according to the invention have a good affinity for the $M_1$-type receptors and a marked specificity for the $M_1$-type central receptors compared with the $M_2$-type peripheral receptors.

By way of example, the compound SR 96181 showed a 50% inhibitory concentration, expressed in micromel, of 0.03 on the ligand for the $M_1$ receptors and 0.35 on the ligand for the $M_2$ receptors.

Likewise, the compound SR 96204 A showed 50% inhibitory concentrations of 0.75 and 50 on the ligand for the $M_1$ and $M_2$ receptors respectively.

In vivo, the compounds according to the invention were subjected to the test for the rotations induced by pirenzepine, described by Worms P. et al. (Psychepharmacology, 1987, 93, 489–493), with the modification that oral administration of the products took place 4 hours before instead of 30 minutes before the injection of pirenzepine.

At a dose of 3 mg per kg of body weight, the products according to the invention strongly inhibit the number of rotations induced by pirenzepine.

Thus, by way of example, the compounds SR 96181 and SR 96204 A inhibit the rotations induced by pirenzepine to the extent of 71% and 67% respectively.

Furthermore, the results obtained with various compounds of formula (IA) will be found in Table 5.

This Table shows the results obtained with the only compound of French patent n° 2 510 998 substituted by an alkyl group in the 5-position and described in said patent as an antidepressant.

This compound has the formula

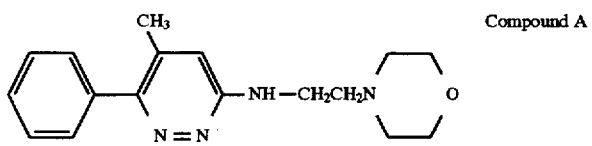

Compound A

TABLE 5A

| Product n° | % inhibition of pirenzepine-induced rotations at a dose of 3 mg/kg per os |
|---|---|
| SR 96197 A | −70%** |
| SR 96224 A | −59%** |
| SR 96231 A | −40%** |
| SR 96232 A | −40%** |
| SR 96223 A | −74%** |
| SR 96230 A | −41%** |
| SR 45964 A | −38%** |
| Compound A | −20%* |

Student t test
*p < 0.05
**p < 0.01

At a dose of 3 mg/kg per os, the compounds according to the invention inhibit the number of rotations induced by pirenzepine with an intensity 2 to 3.5 times greater than the compound of the prior art.

Finally, the compounds according to the invention showed no signs of toxicity at the doses at which they are active.

Consequently, the compounds (IA) can be used as drugs.

The results indicated make it possible to consider using the products according to the invention in all cases where a cholinergic deficiency is evident, especially for the treatment of memory and cognitive disorders and degenerative syndromes associated with senescence and with senile dementia.

According to another of its features, the present patent application therefore relates to pharmaceutical compositions in which at least one of the compounds of formula (IA) or one of their pharmaceutically acceptable salts is present as the active ingredient.

In the pharmaceutical compositions of the present invention for oral, sublingual, percutaneous or rectal administration, the active ingredients of formula (IA) above can be administered to humans in unit forms of administration, mixed with the conventional pharmaceutical excipients, especially for the treatment of senile dementia. Appropriate unit forms of administration include forms for oral administration, such as tablets, gelatin capsules, powders, granules and solutions or suspensions to be taken orally, forms for sublingual and buccal administration, forms for subcutaneous, intramuscular or intravenous administration and forms for rectal administration.

To obtain the desired effect, the dose of active principle can vary between 20 and 500 mg per day.

Each unit dose can contain from 5 to 200 mg of active ingredient in combination with a pharmaceutical excipient. This unit dose can be administered 1 to 4 times a day.

If a solid composition in the form of tablets is prepared, the main active ingredient is mixed with a pharmaceutical vehicle such as gelatin, starch, lactose, magnesium stearate, talc, gum arabic or the like. The tablets can be coated with sucrose or other appropriate substances or they can be treated so as to have a prolonged or delayed activity and so as to release a predetermined amount of active principle continuously.

A preparation in the form of gelatin capsules is obtained by mixing the active ingredient with a diluent and pouring the resulting mixture into soft or hard gelatin capsules.

Water-dispersible granules or powders can contain the active ingredient mixed with dispersants or wetting agents or with suspending agents such as polyvinylpyrrolidone, as well as with sweeteners or taste correctors.

Rectal administration is effected using suppositories which are prepared with binders melting at the rectal temperature, for example cacao butter or polyethylene glycols.

Parenteral administration is effected using aqueous suspensions, isotonic saline solutions or sterile and injectable solutions which contain pharmacologically compatible diapersants and/or wetting agents, examples being propylene glycol and burylone glycol.

The active principle can also be formulated as microcapsules, if appropriate with one or more excipients or additives.

As pharmaceutical preparations, it is possible to prepare the following gelatin capsules:

EXAMPLE 81A

| SR 96204 A | 0.010 g |
|---|---|
| Lactose | 0.050 g |
| Magnesium stearate | 0.005 g |

The above ingredients are intimately mixed and the mixture is poured into hard gelatin capsules.

EXAMPLE 82A

| SR 96187 A | 0.010 g |
|---|---|
| Lactose | 0.005 g |
| Magnesium stearate | 0.05 g |

Pyridazine derivatives have been proposed as drugs for many years, especially those which are active on the cardiovascular system or the central nervous system.

In particular, French patent 2 510 998 and European patent 72 726 disclose pyridazine derivatives which are variously substituted on the pyridazine ring and which all carry, in the 3-position, an amine substituent of the type

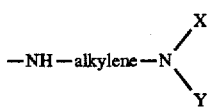

in which X and Y are independently hydrogen or an alkyl group or form, with the nitrogen atom to which they are bonded, a heterocycle such as morpholine.

All these compounds are active on the central nervous system as antidepressants.

According to a third aspect of the present invention, it has now been found that by modifying the substituents on the pyridazine ring, compounds are obtained which have lost their antidepressant activity and acquired a valuable activity as $M_1$-type cholinergic receptor ligands.

The present invention thus also relates to novel pyridazine derivatives of the formula

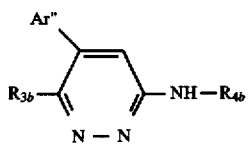

in which

Ar" is a phenyl group of the formula

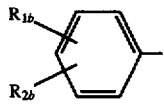

a pyridyl group or a thienyl group;

$R_{1b}$ and $R_{2b}$ are each independently hydrogen, a halogen atom, a hydroxyl group, a $C_1$–$C_4$ alkyl group, a $C_1$–$C_4$ alkoxy or the trifluoromethyl group;

$R_{3b}$ is a linear or branched $C_1$–$C_5$ alkyl, a group —$CH_2$— $C_6H_5$ or a group —$CH_2$—$CH_2$—$C_6H_5$; and $R_{4b}$ is the group

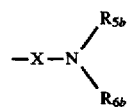

in which

X is a linear or branched $C_1$–$C_6$ alkylene and especially either a group —$(CH_2)_n$—, in which n is an integer from 1 to 3;

or a group

—CH$_2$—C(X$_1$)(X$_1$)—(CH$_2$)$_{n1}$— in which $n_1$ is 0 or 1 and $X_1$ is a $C_1$–$C_3$ alkyl group; and $R_{5b}$ and $R_{6b}$ are each independently hydrogen or a linear or branched $C_1$–$C_4$ alkyl or form, with the nitrogen atom to which they are bonded, a heterocycle selected from pyrrolidine, morpholine or piperidine; or $R_{4b}$ is a group selected from

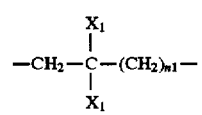

in which n is as defined above and $R_{7b}$ is hydrogen or a $C_1$–$C_4$, preferably $C_1$–$C_2$, alkyl group;

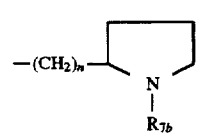

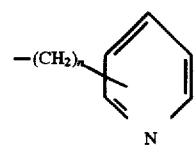

in which n is as defined above,

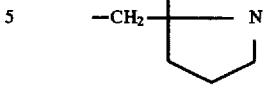

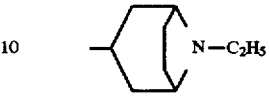

or

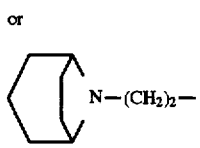

and to their salts with mineral or organic acids.

The salts of the compounds of formula (IB) according to the present invention include both those with mineral or organic acids which permit appropriate separation or crystallization of the compounds of formula (IB), such as picric acid or oxalic acid, and those with mineral or organic acids which form pharmaceutically acceptable salts such as the hydrochloride, hydrobromide, sulfate, hydrogensulfate, dihydrogenphosphate, methanesulfonate, methylsulfate, maleate, fumarate or naphthalene-2-sulfonate.

According to another feature, the present invention relates to a method of preparing the compounds of formula (IB), which comprises reacting a 3-chloropyridazine of the formula

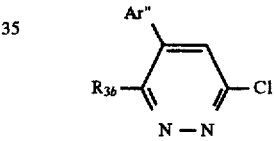

in which Ar" and $R_{3b}$ are as defined above, with an amine of the formula

$R_{4b}NH_2$ in which $R_{4b}$ is as defined above, to give the compounds (IB) according to the invention and, if desired, converting the resulting compound to a salt with a mineral or organic acid.

The substitution reaction of the 3-chloropyridazine (IIB) with the amine $R_{4b}NH_2$ is carried out at a temperature of between 100° and 150° C., in the absence of a solvent or in the presence of an inert solvent such as n-butanol.

The resulting product of formula (IB) is isolated, in the form of the free base or a salt, by the conventional techniques.

When the compound of formula (IB) is obtained in the form of the free base, conversion to a salt is effected by treatment with the chosen acid in an organic solvent. Treatment of the free base, for example dissolved in an alcohol such as isopropanol, with a solution of the chosen acid in the same solvent gives the corresponding salt, which is isolated by the conventional techniques. The hydrochloride, hydrobromide, sulfate, hydrogensulfate, dihydrogenphosphate, methanesulfonate, methylsulfate, oxalate, maleate, fumarate or naphthalene-2-sulfonate, for example, is prepared in this way.

When the reaction is complete, the compound of formula (IB) can be isolated in the form of one of its salts, for example the hydrochloride, oxalate or fumarate. In this case, if necessary, the free base can be prepared by neutralization of said salt with a mineral or organic base such as sodium hydroxide or triethylamine, or with an alkali metal carbonate or bicarbonate such as sodium or potassium carbonate or bicarbonate.

When $R_{1b}$ and/or $R_{2b}$ are a hydroxyl group, the compound according to the invention is obtained from the compound (IB) in which $R_{1b}$ and/or $R_{2b}$ are an alkoxy, all the other substituents being as defined above, by dealkylation using known methods.

The 3-chloropyridazines (IIB) used as starting materials are prepared from the 2H-pyridazin-3-ones (IIIB) of the formula

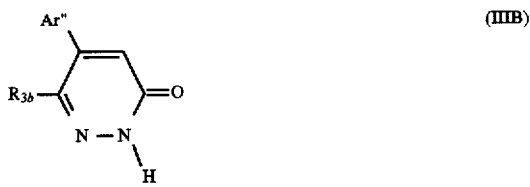
(IIIB)

by reaction with excess phosphorus oxychloride under the action of heat, without a solvent or in the presence of an inert solvent such as acetonitrile.

The 2H-pyridazin-3-ones (IIIB) above are obtained by dehydrogenation of the compounds of formula (IVB):

(IVB)

for example by reaction with bromine in acetic acid.

The 2,3,4,5-tetrahydropyridazin-3-ones of the formula

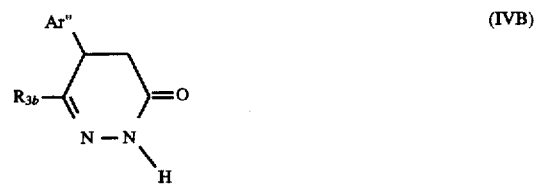
(IVB)

and the 2,3-dihydropyridazin-3-ones of formula (IIIB), which are novel and form part of the invention, are prepared by the methods described by SUTTER et al., J. Am. Chem. Soc., 1942, 64, 533–536, MUKHIRJI D., Science and Culture, 1948, 13, 426, and PINNA G. et al., Il Farmaco, Ed. Sci., 1988, 43, 539–549.

The intermediates of the formulae

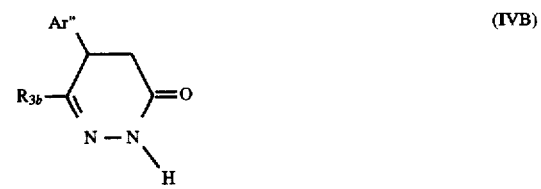
(IVB)

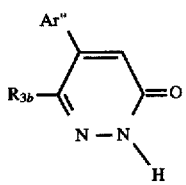
(IIIB)

in which Ar" and $R_{3b}$ are as defined above, which are useful for the preparation of (IB), are novel and form part of the invention with the exception of the compounds in which Ar" is an unsubstituted phenyl and $R_{3b}$ is a methyl group. By way of example, compounds of formulae (IVB) and (IIIB) are described in Tables 1B and 2B below.

The chlorinated compounds of formula (IIB):

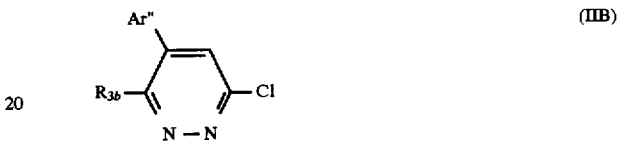
(IIB)

which are novel and form part of the invention, are prepared by the customary methods. By way of example, compounds of formula (IIB) are described in Table 3B below.

Substitution of these chlorinated compounds (IIB) with an amine makes it possible to obtain the compounds (IB), the preparation of which is illustrated by the reaction scheme below.

SCHEME 1B

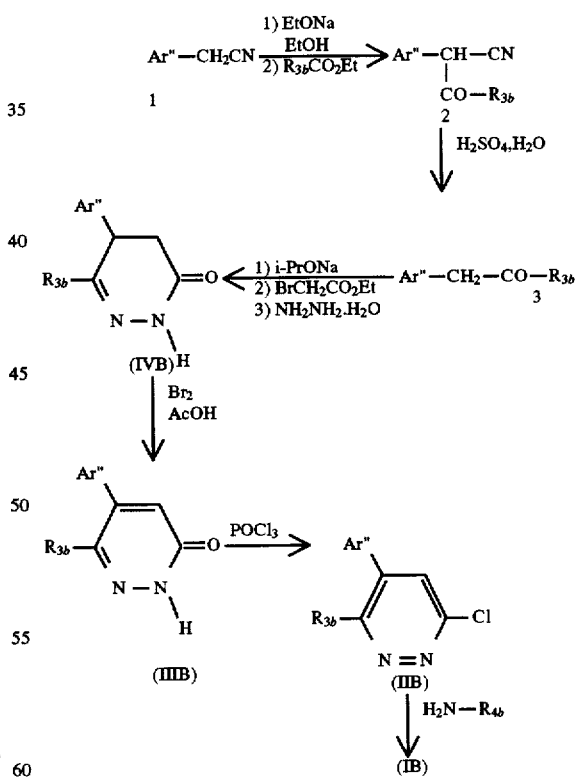

Heating a nitrile 1 in the presence of a base and a carboxylic acid ester derivative $R_{3b}CO_2Et$ gives the β-ketonitrile 2, which is converted to the corresponding ketone derivative 3 in an acidic medium.

Cyclization to the 2,3,4,5-tetrahydropyridazin-3-one is effected by reaction with ethyl bromoacetate in an alcoholic solvent at room temperature, followed by reaction with hydrazine hydrate under the action of heat.

Dehydrogenation of the compound (IVB) by reaction with bromine in acetic acid makes it possible to prepare the 2,3-dihydropyridazin-3-one (IIIB).

In the case where $n_1=0$, the amines

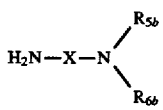

in which X is a group

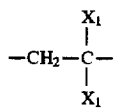

in which $X_1$ is as defined above, are prepared from a cyano derivative of the formula

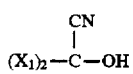

by reaction with an amine of the formula $HNR_5R_6$, if appropriate in the presence of a salt of a strong acid, such as sodium or magnesium sulfate, at a temperature of between 40° and 80° C., to give the aminonitrile of the formula

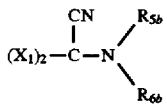

which is hydrated under the customary conditions, in an acidic medium, to give the corresponding amide of the formula

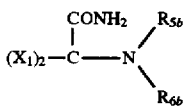

which is then reduced by reaction with a metal hydride, such as lithium aluminum hydride or boron hydride, to give the expected amine

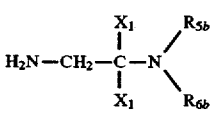

The following Examples illustrate the invention without however implying a limitation.

EXAMPLE 1B 3-(2-Diethylamino-2-methylprop-1-yl)amino-5-(4-fluorophenyl)-6-propylpyridazine A) α-Butyryl-4-fluorophenylacetonitrile 10.9 g of sodium are added to 150 ml of absolute ethanol. While maintaining reflux, a solution of 49.5 g of 4-fluorophenylacetonitrile in 65.2 g of ethyl butyrate is added. The reaction mixture is refluxed for 4 hours and then left to stand overnight at room temperature. The solvents are concentrated under vacuum and the residue is taken up in water and washed with ether. The aqueous phase is cooled in an ice bath and acidified to pH 5–6 by the addition of concentrated acetic acid to give crystals, which are filtered off, washed with water and dissolved in methylene chloride.

The organic phase is decanted, dried over $MgSO_4$, filtered and concentrated under vacuum.

m=50 g

M.p.=53°–54° C.

B) 1-(4-Fluorophenyl)pentan-2-one 50 g of the product obtained above are treated with 36 ml of water and 148 ml of concentrated sulfuric acid, which is added dropwise at 4° C., with stirring. The mixture is then heated at 80° C. for ½ hour and cooled, 534 ml of water are then added and the mixture is refluxed overnight.

The mixture is extracted with methylene chloride and the organic phase is decanted, dried over $Na_2SO_4$, filtered and concentrated under vacuum.

The residue is chromatographed on silica gel using 50/50 cyclohexane/methylene chloride as the eluent.

m=39.2 g

C) 5-(4-Fluorophenyl)-6-propyl-2,3,4,5-tetrahydropyridazin-3-one 2.76 g of sodium are dissolved in 115 ml of isopropanol. A solution of 21.56 g of the product obtained above in 30 ml of isopropanol is added, with cooling in an ice bath. The mixture is stirred for one hour at room temperature, a solution of 15 ml of ethyl bromoacetate in 20 ml of isopropanol is then added dropwise and the mixture is left to stand at room temperature for 24 hours.

The residue is taken up in acidified water (HCl–pH=2) and extracted with methylene chloride. The organic phase is decanted and dried over $MgSO_4$. It is filtered and concentrated under vacuum. The residue is taken up in 75 ml of butanol, 11.25 ml of hydrazine hydrate are added and the reaction mixture is refluxed for 4 hours.

The mixture is concentrated under vacuum and the residue is taken up in water and extracted with methylene chloride. The organic phase is decanted, dried over $MgSO_4$, filtered and concentrated under vacuum.

m=13.7 g

M.p.=78°–79° C.

D) 2,3-Dihydro-5-(4-fluorophenyl)-6-propylpyridazin-3-one 9.37 g of the product obtained above are dissolved in 40 ml of acetic acid and heated to 80° C. A solution of 7.6 g of bromine in 70 ml of acetic acid is then added dropwise and the reaction mixture is refluxed for 4 hours. It is cooled to 15° C. and a precipitate is filtered off.

m=6.6 g

M.p.=193°–194° C.

E) 3-Chloro-5-(4-fluorophenyl)-6-propylpyridazine 4.64 g of the product obtained above are dissolved in 28 ml of acetonitrile and 8.6 ml of phosphorus oxychloride and the reaction mixture is refluxed for 4 hours and then concentrated under vacuum. The residue is taken up in iced water, aqueous ammonia is added and the mixture is then extracted with methylene chloride. The organic phases are decanted, dried over $MgSO_4$, filtered and concentrated under vacuum. The residue is chromatographed on silica gel using 95/5 methylene chloride/ethyl acetate as the eluent.

m=4.35 g

M.p.=64° C.

F) Compound 1B 1 g of the product obtained above and 3 g of 1-amino-2-diethylamino-2-methylpropane are heated at 120° C., under nitrogen, for 48 hours.

The mixture is concentrated under vacuum and the residue is taken up in a 5% solution of sodium carbonate and extracted with methylene chloride. The organic phase is decanted, dried over MgSO$_4$, filtered and concentrated under vacuum. The residue is chromaographed on Merck H silica gel using 96/4 methylene chloride/methanol as the eluent.

The pure product fractions are concentrated under vacuum, the residue is taken up in ether and the addition of a solution of hydrogen chloride in ether makes it possible to prepare the hydrochloride, which is filtered off.

m=1.4 g

M.p.=100°–115° C.

EXAMPLES 2B to 19B

A) The 2,3,4,5-tetrahydropyridazin-3-ones listed in Table 1B below are obtained by following the procedure described in Example 1B, steps A, B and C, except that the starting nitrile is replaced with another nitrile derivative, where appropriate, and the carboxylic acid ester is varied.

TABLE 1B

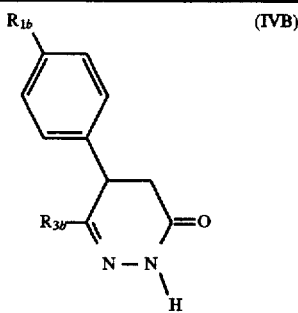

(IVB)

| $R_{1b}$ | $R_{3b}$ | M.p.; °C. | Recrystallization solvent |
|---|---|---|---|
| H | —CH$_2$CH$_3$ | 131–132 | hexane |
| H | n-C$_3$H$_7$ | 104–105 | hexane |
| H | i-C$_3$H$_7$ | 137–138 | heptane |
| H | n-C$_4$H$_9$ | 92–93 | hexane |
| H | neopentyl | 155–156 | hexane |
| H | —CH$_2$—C$_6$H$_5$ | 114–115 | hexane |
| H | —CH$_2$—CH$_2$—C$_6$H$_5$ | 142–143 | Et$_2$O |
| F | n-C$_3$H$_7$ | 78–79 | heptane |
| F | i-C$_4$H$_9$ | 106.5–107.5 | Et$_2$O |
| Cl | —CH$_3$ | 160–161 | Et$_2$O |
| Cl | —CH$_2$CH$_3$ | 121–122 | hexane |
| Cl | n-C$_3$H$_7$ | 118–119 | heptane |

B) The 2,3-dihydropyridazin-3-ones listed in Table 2B below are obtained from the derivatives in Table 1B in the manner described in Example 1B, step D, by reaction with bromine followed by dehydrohalogenation. These compounds were all recrystallized from a methylene chloride/hexane mixture.

TABLE 2B

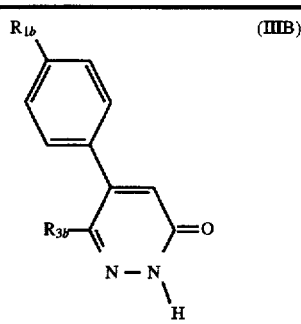

(IIIB)

| $R_{1b}$ | $R_{3b}$ | M.p.; °C. |
|---|---|---|
| H | —CH$_2$CH$_3$ | 123–124 |
| H | n-C$_3$H$_7$ | 162–163 |
| H | i-C$_3$H$_7$ | 178–179 |
| H | i-C$_4$H$_9$ | 154–155 |
| H | neopentyl | 181–182 |
| H | —CH$_2$—C$_6$H$_5$ | 140–141 |
| H | —CH$_2$—CH$_2$—C$_6$H$_5$ | 169–170 |
| F | n-C$_3$H$_7$ | 193–194 |
| F | i-C$_4$H$_9$ | 194–195 |
| Cl | —CH$_3$ | 212–214 |
| Cl | —CH$_2$CH$_3$ | 206–207 |
| Cl | n-C$_3$H$_7$ | 187–188 |

C) The chlorinated derivatives are prepared from the derivatives in Table 2B by reaction with phosphorus oxychloride in the manner described in Example 1B, step E. These chlorine derivatives, which are listed in Table 3B below, were all recrystallized from methylene chloride.

TABLE 3B

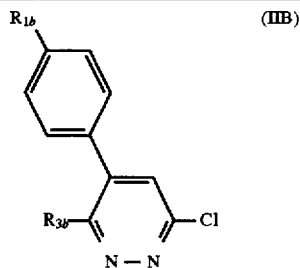

(IIB)

| $R_{1b}$ | $R_{3b}$ | M.p.; °C. |
|---|---|---|
| H | —CH$_2$CH$_3$ | 49 |
| H | n-C$_3$H$_7$ | 58 |
| H | i-C$_3$H$_7$ | 86–87 |
| H | i-C$_4$H$_9$ | 70–71 |
| H | neopentyl | 99–100 |
| H | —CH$_2$—C$_6$H$_5$ | 99 |
| H | —CH$_2$—CH$_2$—C$_6$H$_5$ | 94–95 |
| F | n-C$_3$H$_7$ | 64 |
| F | i-C$_4$H$_9$ | oil |
| Cl | —CH$_3$ | 127–128 |
| Cl | —CH$_2$CH$_3$ | 84–85 |
| Cl | n-C$_3$H$_7$ | 63 |

D) Substitution of the chlorinated derivatives with an amine, according to Example 1B, step F, makes it possible to prepare the compounds (IB) according to the invention, which are listed in Tables 4B, 5B and 6B below.

TABLE 4B (IB)

[Structure: 4-R_{1b}-phenyl substituted pyridazine with R_{3b}, and NH—(CH_2)_n—NR_{5b}R_{6b}]

| Example | R_{1b} | R_{3b} | n | —N(R_{5b})(R_{6b}) | M.p.; °C. Recrystallization solvent | Salt |
|---|---|---|---|---|---|---|
| 2B | H | —CH_3 | 2 | —N—(C_2H_5)_2 | 88 hexane | base |
| 3B | H | n-C_3H_7 | 2 | —N—(C_2H_5)_2 | 129 EtOH | fumarate |
| 4B | H | —CH_3 | 2 | —N(piperidine) | 241 EtOH | 2HCl |
| 5B | H | —CH_3 | 2 | —N(morpholine) | 93 hexane | base |
| 6B | Cl | n-C_3H_7 | 3 | —N—(C_2H_5)_2 | 58 hexane | base |

TABLE 5B (IB)

[Structure: 4-R_{1b}-phenyl substituted pyridazine with R_{3b}, and NH—R_{4b}]

| Example | R_{1b} | R_{3b} | R_{4b} | M.p.; °C. Recrystallization solvent | Salt |
|---|---|---|---|---|---|
| 7B | H | —CH_3 | N-ethylpyrrolidin-2-yl-CH_2— | 154 acetone | sesquifumarate |
| 8B | H | n-C_3H_7 | N-ethylpyrrolidin-2-yl-CH_2— | 154 Et_2O | sesquifumarate |
| 9B | H | n-C_3H_7 | pyridin-2-yl-CH_2— | 171 Et_2O | 2HCl |

TABLE 5B-continued
(IB)
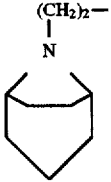
| Example | $R_{1b}$ | $R_{3b}$ | $R_{4b}$ | M.p.; °C. Recrystallization solvent | Salt |
|---|---|---|---|---|---|
| 10B | H | $-C_2H_5$ | 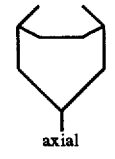 | 90 Et$_2$O | 2HCl |
| 11B | H | $CH_3$ | 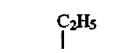 | 162.5 Et$_2$O | difumarate |
| 12B | H | $CH_3$ | 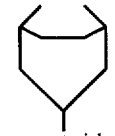 | 169.2 iPrOH | trifumarate |
| 13B | H | i-$C_4H_9$ | $C_2H_5$ N axial | 99 Et$_2$O—iPrOH | difumarate hemihydrate |
| 14B | H | i-$C_4H_9$ | $C_2H_5$ N equatorial | 151 Et$_2$O—iPrOH | difumarate |

TABLE 6B

Structure: Phenyl-pyridazine with R1b on phenyl, R3b on pyridazine, linked via NH-CH2-C(CH3)2-N(R5b)(R6b)

| Example | R1b | R3b | -N(R5b)(R6b) | M.p.; °C. Recrystallization solvent | Salt |
|---|---|---|---|---|---|
| 15B | H | -CH3 | -N-(C2H5)2 | 132-134 acetone | fumarate ½H2O |
| 16B | H | -C2H5 | -N-(C2H5)2 | 95 Et2O | difumarate |
| 17B | H | n-C3H7 | -N-(C2H5)2 | 121 Et2O | difumarate |
| 18B | H | i-C3H7 | -N(C2H5)2 | 164-165 i-PrOH | sesquifumarate |
| 19B | H | i-C4H9 | -N(C2H5)2 | 148-149 Et2O | difumarate |
| 20B | H | -CH2-C6H5 (CH2-phenyl) | -N-(C2H5)2 | 115 Et2O | 2HCl |
| 21B | H | -CH2-t-Bu | -N(C2H5)2 | 114-115 Et2O | 2HCl |
| 22B | H | -(CH2)2-C6H5 | -N(C2H5)2 | 110 Et2O | 2HCl |
| 23B | F | i-C4H9 | -N-(C2H5)2 | 161-162 Et2O | sesquifumarate |
| 24B | Cl | -CH3 | -N-(C2H5)2 | 100-105 Et2O | 2HCl |
| 25B | Cl | -C2H5 | -N-(C2H5)2 | 95-100 Et2O | 2HCl |
| 26B | Cl | n-C3H7 | -N-(C2H5)2 | 134-135 Et2O | difumarate |

The compounds according to the invention were studied for their pharmacological properties and in particular for their affinity for the $M_1$-type and $M_2$-type muscarinic cholinergic receptors.

In vitro, the compounds (IB) were tested according to the technique described by L. POTTER et al., J. Pharmacol. Exp. Ther., 1989, 284, 974–978, for their affinity for the $M_1$-type receptors, and according to the technique described by HAMMER R. et al., Life Science, 1986, 38, 1653–1662, for their affinity for the $M_2$-type receptors.

The compounds according to the invention have a good affinity for the $M_1$-type receptors and a marked specificity for the $M_1$-type central receptors compared with the $M_2$-type receptors.

By way of example, compound 6B showed 50% inhibitory concentrations, expressed in micromol, of 0.16 and 1.5 on the $M_1$ and $M_2$ receptors respectively.

Likewise, compound 25B showed 50% inhibitory concentrations of 0.04 and 0.9 on the $M_1$ and $M_2$ receptors respectively.

In vivo, the compounds according to the invention were subjected to the test for the rotations induced by intrastriatal pirenzepine, described by Worms P. et al., Psychopharmacology, 1987, 93, 489–493.

At a dose of 3 mg per kg of body weight, administered orally, the products according to the invention strongly inhibit the number of rotations induced by pirenzepine. Thus, by way of example, compound 6B causes a 71% inhibition of the rotations induced by pirenzepine.

Furthermore, the compounds according to the invention have proved to be active on the memory deficiency induced by scopolamine and pentetrazole in the passive avoidance test on rats, described by WORMS P. et al., Psychopharmacol., 1989, 98, 286–288.

Thus the results of this test show that compound 6B according to the invention opposes the amnesia induced by pirenzepine administered intraperitoneally at a dose of 75 mg/kg, with an $ED_{50}$ of 0.47 mg/kg, administered orally.

Finally, the compounds according to the invention showed no signs of toxicity at the doses at which they are active.

Consequently, the compounds (IB) can be used as drugs.

The results indicated show that the compounds according to the invention have a good affinity for the muscarinic receptors and a good activity in the tests for amnesia induced by scopolamine or pirenzepine. They make it possible to consider using the products according to the invention in all cases where a cholinergic deficiency is evident, especially for the treatment of cognitive memory disorders and degenerative syndromes associated with senescence and with senile dementia.

According to another feature, the present patent application therefore relates to the pharmaceutical compositions in which at least one of the compounds of formula (IB) or one of their salts is present as the active principle.

In the pharmaceutical compositions of the present invention for oral, sublingual, transdermal or rectal administration, the active principles of formula (IB) above can be administered to humans in unit forms of administration, mixed with the conventional pharmaceutical carriers, especially for the treatment of cognitive memory disorders or degenerative syndromes. Appropriate unit forms of administration include forms for oral administration, such as tablets, gelatin capsules, powders, granules and solutions or suspensions to be taken orally, forms for sublingual and buccal administration, forms for subcutaneous, intramuscular or intravenous administration and forms for rectal administration.

To obtain the desired effect, the dose of active principle can vary between 5 and 1000 mg per day.

Each unit dose can contain from 5 to 200 mg of active ingredient in combination with a pharmaceutical carrier. This unit dose can be administered 1 to 5 times a day.

If a solid composition in the form of tablets is prepared, the main active principle is mixed with a pharmaceutical vehicle such as gelatin, starch, lactose, magnesium stearate, talc, gum arabic or the like. The tablets can be coated with sucrose or other appropriate substances or they can be treated so as to have a prolonged or delayed activity and so as to release a predetermined amount of active principle continuously.

A preparation in the form of gelatin capsules is obtained by mixing the active principle with a diluent and pouring the resulting mixture into soft or hard gelatin capsules.

Water-dispersible granules or powders can contain the active principle mixed with dispersants or wetting agents or with suspending agents such as polyvinylpyrrolidone, as well as with sweeteners or taste correctors.

Rectal administration is effected using suppositories which are prepared with binders melting at the rectal temperature, for example cacao butter or polyethylene glycols.

Parenteral administration is effected using aqueous suspensions, isotonic saline solutions or sterile and injectable solutions which contain pharmaceutically compatible dispersants and/or wetting agents, for example propylene glycol and butylene glycol.

The active principle can also be formulated as microcapsules, if appropriate with one or more carriers or additives.

As a pharmaceutical preparation, it is possible to prepare gelatin capsules containing

| | |
|---|---|
| Compound 6B | 0.010 g |
| Lactose | 0.050 g |
| Magnesium stearate | 0.005 g | by intimately mixing the above ingredients and pouring the mixture into hard gelatin capsules.

We claim:
1. A compound of the formula

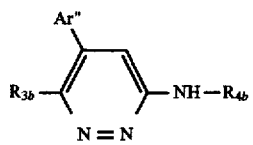

(Ib)

in which

Ar" is a phenyl group of the formula

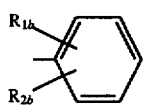

a pyridyl group or a thienyl group;

$R_{1b}$ and $R_{2b}$ are each independently hydrogen, a halogen atom, a hydroxyl group, a $C_1$–$C_4$ alkyl group, a $C_1$–$C_4$ alkoxy or the trifluoromethyl group;

$R_{3b}$ is a linear or branched $C_1$–$C_5$ alkyl, a group —$CH_2$—$C_6H_5$ or a group —$CH_2$—$CH_2$—$C_6H_5$; and $R_{4b}$ is the group

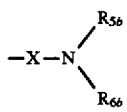

in which

X is a linear or branched $C_1$–$C_6$ alkylene and $R_{5b}$ and $R_{6b}$ form, with the nitrogen atom to which they are bonded, a pyrrolidine or piperidine; or $R_{4b}$ is a group selected from

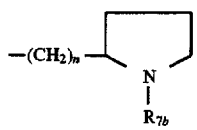

in which n is an integer from 1 to 3 and $R_{7b}$ is hydrogen or a $C_1$–$C_4$ group; and

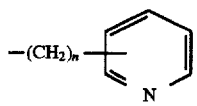

in which n is as defined above, or its salts which are pharmaceutically acceptable or permit crystallization thereof.

2. A compound according to claim 1, wherein $R_{4b}$ represents —$XNR_{5b}R_{6b}$ in which:

X represents either a group —$(CH_2)_n$—, in which n is an integer from 1 to 3;

or a group

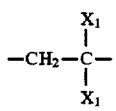

in which $X_1$ is a methyl or ethyl group; and $R_{5b}$ and $R_{6b}$ are as defined in claim 1, or its salts which are pharmaceutically acceptable or permit crystallization thereof.

3. A compound according to claim 1, wherein $R_{4b}$ represents a group

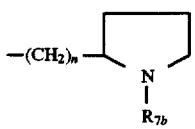

in which $R_{7b}$ is a ($C_1$–$C_2$)alkyl group and n is as defined in claim 1, or its salts which are pharmaceutically acceptable or permit crystallization thereof.

4. A pharmaceutical composition comprising (i) an effective amount of a compound according to claim 1 or a pharmaceutically acceptable salt thereof and (ii) suitable excipients.

5. A pharmaceutical composition comprising (i) an effective amount of a compound according to claim 2, and (ii) suitable excipients.

6. A pharmaceutical composition comprising (i) an effective amount of a compound according to claim 3, and (ii) suitable excipients.

7. A compound of formula:

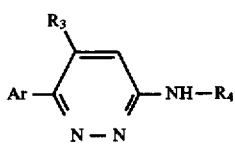
(I)

in which:

Ar represents a phenyl group substituted by $R_1$ and $R_2$, a pyridyl group or a thienyl group;

$R_1$ and $R_2$ each independently represents hydrogen, halogen, trifluoromethyl, hydroxyl, ($C_1$–$C_4$)alkoxy or ($C_1$–$C_4$)alkyl;

$R_3$ represents a ($C_1$–$C_4$)alkyl, a ($C_3$–$C_7$)cycloalkyl or the Ar' radical, Ar' being phenyl substituted by $R_1$ and $R_2$;

$R_4$ represents (a) a group

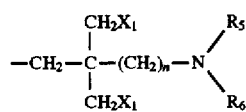

in which $X_1$ represents hydrogen or methyl;
n is 0; and
$R_5$ and $R_6$ form, with the nitrogen atom to which they are bonded, a pyrrolidine or a piperidine;

(b) a group

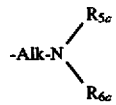

in which Alk is a ($C_1$–$C_6$)alkylene group and $R_{5a}$ and $R_{6a}$ form, with the nitrogen atom to which they are bonded, a pyrrolidine, a N-methylpiperazine or a piperidine which is unsubstituted or substituted by one or more methyl groups, by a hydroxyl, by a phenyl or by a benzyl;

(c) a group

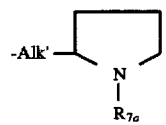

in which Alk' is a ($C_1$–$C_3$)alkylene group and $R_{7a}$ is a ($C_1$–$C_4$)alkyl group;

(d) or a group

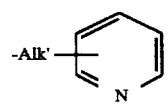

in which Alk' is as defined above and substitutes the pyridine in the 2-,3- or 4-position, with the proviso that $R_3$ is ($C_3$–$C_7$)cycloalkyl or substituted phenyl only when $R_4$ is the group —$CH_2$—$C(CH_2X_1)$—$(CH_2)_n$—$NR_5R_6$;

or its salts which are pharmaceutically acceptable or permit crystallization thereof.

8. A compound according to claim 7 in which Ar is the group

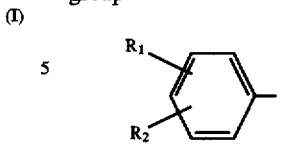

wherein $R_1$ and $R_2$ are as defined in claim 7, and $R_4$ is either group (b), (c) or (d), or its salts which are pharmaceutically acceptable or permit crystallization thereof.

9. A compound according to claim 8 of the formula:

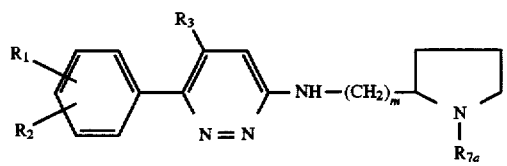

in which $R_1$, $R_2$, $R_3$ and $R_{7a}$ are as defined in claim 7 and m is 1, 2 or 3, or its salts which are pharmaceutically acceptable or permit crystallization thereof.

10. A compound according to claim 9, wherein m is equal to 1 or 2, or its salts which are pharmaceutically acceptable or permit crystallization thereof.

11. A pharmaceutical composition comprising (i) an effective amount of a compound according to claim 7 or a pharmaceutically acceptable salt thereof and (ii) suitable excipients.

12. A pharmaceutical composition comprising (i) an effective amount of a compound according to claim 8, and (ii) suitable excipients.

13. A pharmaceutical composition comprising (i) an effective amount of a compound according to claim 9, and (ii) suitable excipients.

14. A pharmaceutical composition comprising (i) an effective amount of a compound according to claim 10, and (ii) suitable excipients.

15. A compound of formula (Ib)

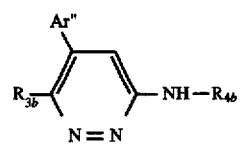
(Ib)

in which:

Ar" is a phenyl group of formula

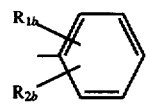

a pyridyl group or a thienyl group;

$R_{1b}$ and $R_{2b}$ are each independently hydrogen, a halogen atom, a hydroxyl group, a $C_1$–$C_4$ alkyl group, a $C_1$–$C_4$ alkoxy group or a trifluoromethyl group;

$R_{3b}$ is a linear or branched $C_1$–$C_5$ alkyl group, a group —$CH_2$—$C_6H_5$ or a group —$CH_2$—$CH_2$—$C_6H_5$; and $R_{4b}$ is a group

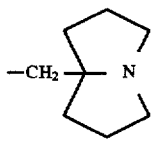

or its salts which are pharmaceutically acceptable or permit crystallization thereof.

16. A compound according to claim 15, which is 3-[1-azabicyclo[3.3.0]oct-5-ylmethyl]amino-6-methyl-5-phenylpyridazine or its salts which are pharmaceutically acceptable or permit crystallization thereof.

17. A pharmaceutical composition comprising (i) an effective amount of a compound according to claim 15 or a pharmaceutically acceptable salt thereof and (ii) suitable excipients.

18. A pharmaceutical composition comprising (i) an effective amount of a compound according to claim 16 or a pharmaceutically acceptable salt thereof and (ii) suitable excipients.

* * * * *